United States Patent
Wagner et al.

(10) Patent No.: US 8,535,648 B2
(45) Date of Patent: Sep. 17, 2013

(54) STABILIZATION OF UV-SENSITIVE ACTIVE INGREDIENTS

(75) Inventors: Barbara Wagner, Lörrach (DE); Bernd Herzog, Grenzach-Wyhlen (DE); Stefan Müller, Weil am Rhein (DE); Thomas Ehlis, Freiburg (DE)

(73) Assignee: BASF SE, Ludwigshafen (DE)

( * ) Notice: Subject to any disclaimer, the term of this patent is extended or adjusted under 35 U.S.C. 154(b) by 235 days.

(21) Appl. No.: 12/520,880

(22) PCT Filed: Jan. 16, 2008

(86) PCT No.: PCT/EP2008/050440
§ 371 (c)(1),
(2), (4) Date: Oct. 27, 2009

(87) PCT Pub. No.: WO2008/090066
PCT Pub. Date: Jul. 31, 2008

(65) Prior Publication Data
US 2010/0104523 A1    Apr. 29, 2010

(30) Foreign Application Priority Data
Jan. 25, 2007    (EP) .................................. 07101171

(51) Int. Cl.
*A61K 8/00*    (2006.01)
(52) U.S. Cl.
USPC .............................. 424/60; 424/59; 424/70.9
(58) Field of Classification Search
USPC ........................................... 424/59, 60, 70.9
See application file for complete search history.

(56) References Cited

U.S. PATENT DOCUMENTS

| 7,563,289 | B2 | 7/2009 | Eliu et al. |
| 2005/0255055 | A1 * | 11/2005 | Wagner et al. ................... 424/59 |
| 2009/0100610 | A1 | 4/2009 | Cremer et al. |
| 2009/0130045 | A1 | 5/2009 | Cremer et al. |
| 2009/0151091 | A1 | 6/2009 | Cremer et al. |

FOREIGN PATENT DOCUMENTS

| WO | 2004006878 | 1/2004 |
| WO | 2006003094 | 1/2006 |
| WO | 2006016806 | 2/2006 |
| WO | 2006032741 | 3/2006 |
| WO | 2006125676 | 11/2006 |
| WO | WO-2006/125676 A1 * | 11/2006 |
| WO | 2007014848 | 2/2007 |

OTHER PUBLICATIONS

L. R. Gaspar et al., International Journal of Pharmaceutics, vol. 307, (2006), pp. 123-128.

* cited by examiner

*Primary Examiner* — Ali Soroush
(74) *Attorney, Agent, or Firm* — Shiela A. Loggins

(57) ABSTRACT

Disclosed is the use of merocyanine derivatives of formula (1) for stabilizing UV-sensitive active ingredients like dibenzoylmethane derivatives.

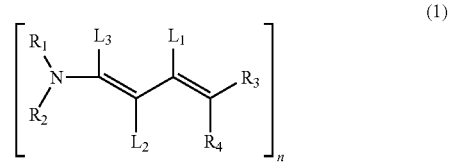

(1)

16 Claims, 1 Drawing Sheet

Stabilization of BMDBM by Merocyanines

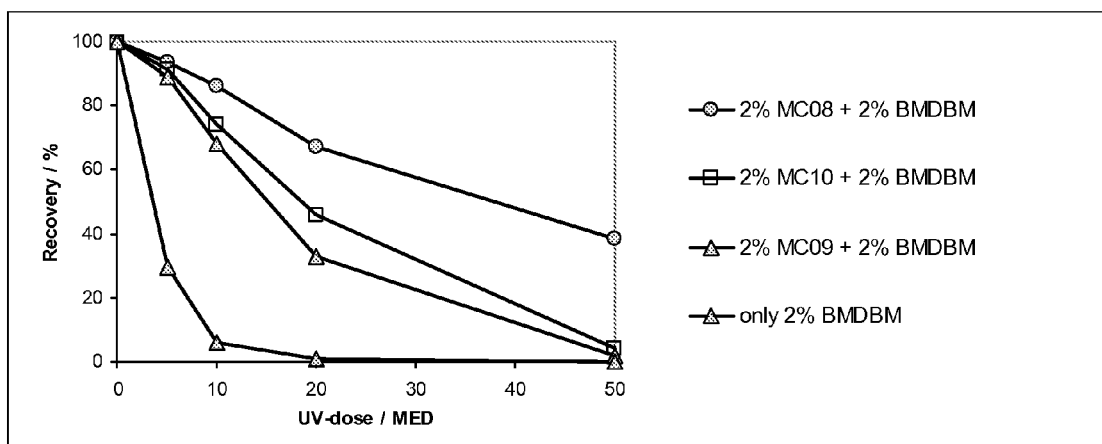
Stabilization of BMDBM by Merocyanines

STABILIZATION OF UV-SENSITIVE ACTIVE INGREDIENTS

It is well known that ultraviolet radiation (light) is harmful to human skin. Depending on the wavelength the UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A and UV-B filter covering the full range of about 290 nm to about 400 nm to prevent the human skin from damaging by the sunlight.

The effects of UV-A are mainly mediated by free radicals, e.g. reactive oxygen species inducing different types of degradation to cellular DNA, lipids, and proteins. The visible signs are often the result of long-term, cumulative effects. This is why skin photoaging is associated with UV-A light. It is also known that normal outdoor UV-A radiation can be effective enough to cause the breakdown of the proteins collagen and elastin leading to a loss of firmness and resilience of the skin. Therefore the UVA protection of a daily skin care is of significant relevance.

Numerous UV-B filters are registered for their use in sunscreen preparations, which are mainly derivatives of the 3-benzylidenecamphor, ethylhexyl salicylates and p-methoxy-cinnamic acid esters, such as 2-ethylhexyl p-methoxycinnamate.

The most commonly used commercial UV-A filter is a dibenzoylmethane derivative, particularly the 4-(tert-butyl)-4'-methoxydibenzoylmethane (also called avobenzone, CAS No. 70356-09-1), which is commercialised by DSM under the brand name Parsol® 1789 and Merck under the brand name Eusolex® 9020. Other dibenzoylmethane derivatives are described in U.S. Pat. Nos. 4,489,057, 4,387,089 and 4,562,067.

Unfortunately, these characteristic UVA absorbing organic compounds employed in sunscreen compositions suffer from relatively rapid photodegradation with the consequence that the protection from sun damage is lost. It is also known that dibenzoylmethane compounds are especially sensitive to UV-A radiation. In general sunscreen preparations formulated with avobenzone as the UV-A shielding agent also contain particular UV stabilizers, e.g. Ethylhexyl-2-cyano-3,3-diphenylacrylate (octocrylene) or 4-methylbenzylidene camphor. Other methods of stabilizing dibenzoylmethane derivatives include the addition of a diester and/or a polyester of naphthalene dicarboxylic acid.

Several cosmetic adjuvants different from UV filters are known which are efficient active ingredients but have low photostability, for example ubichinone, retinoides and carotinoides. The use of these active ingredients in cosmetic and dermatological formulations is desirable, and therefore stabilization would be advantageous.

One challenge of this invention is therefore to enhance the stability of UV-sensitive active ingredients as well as to provide stable cosmetic and dermatological formulations containing UV-sensitive active ingredients whose activities and properties are retained over a long time.

Surprisingly, it has been found that the use of specific merocyanine derivatives absorbing in the UV/Vis region of about 320 nm to about 450 nm will enhance the stability of cosmetic and dermatological formulations comprising at least one UV-sensitive active ingredient.

Therefore, the present invention relates to the use of merocyanine derivatives of formula

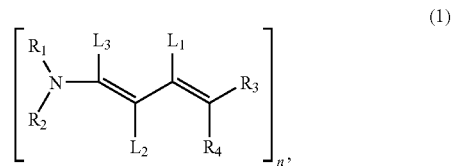

(1)

wherein
$L_1$, $L_2$ or $L_3$ independently of each other hydrogen; hydroxy; $C_1$-$C_{22}$alkyl; $C_1$-$C_{22}$alkoxy; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl, $C_4$-$C_{20}$heteroaralkyl; $C_6$-$C_{18}$aryl;
$R_4$ is CN; —$COR_5$; —$COOR_5$; —$CONR_5R_6$; $C_2$-$C_{22}$alkenyl; $C_2$-$C_{22}$ alkinyl; $C_3$-$C_{12}$cycloalkenyl; $C_6$-$C_{18}$ aryl; $C_2$-$C_{12}$heteroalkyl; $C_3$-$C_5$heterocycloalkyl; or $C_3$-$C_{12}$heteroaryl;
$R_5$, $R_6$, $R_7$ and $R_8$ are independently of each other hydrogen; $C_1$-$C_{22}$alkyl, $C_2$-$C_{22}$alkenyl, $C_2$-$C_{22}$alkinyl; $C_3$-$C_{12}$cycloalkyl; $C_3$-$C_{12}$cycloalkenyl; $C_7$-$C_{20}$ aralkyl; $C_1$-$C_{20}$heteroalkyl; $C_3$-$C_{12}$cycloheteroalkyl; $C_5$-$C_{20}$heteroaralkyl; $C_6$-$C_{18}$ aryl; $C_3$-$C_{12}$heteroaryl; —$(CH_2)_u$—$SiR_{16}R_{17}R_{18}$; or a radical —X-Sil; or
$L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $R_3$ and $R_4$, $R_1$ and $R_2$, $R_5$ and $R_6$, and $R_7$ and $R_8$ may be linked together to form 1, 2, 3 or 4 carbocyclic or heterocyclic rings, which may be uninterrupted or interrupted by one or more —O—, —S— or $NR_9$— and/or which may be further fused with other aromatic rings and/or which may be substituted with one or more $C_1$-$C_6$alkyl groups;
and each alkyl, alkenyl, alkinyl, cycloalkyl or cycloalkylene group may be unsubstituted or substituted by one or more $R_{10}$;
and each aryl, heteroaryl, aralkyl, arylene, heteroarylene or aralkylene may be unsubstituted or substituted by one or more $R_{11}$;
$R_9$ is $R_{12}$; $COR_{12}$, $COOR_{12}$; or $CONR_{12}R_{13}$;
$R_{10}$ is halogen, OH; $NR_{14}R_{15}$; O—$R_{14}$; S—$R_{14}$; CO—$R_{14}$; O—CO—$R_{14}$; oxo; thiono; ($C_1$-$C_6$)alkylidene; CN; $COOR_{14}$; $CONR_{14}R_{14}$; $SO_{15}NR_{14}R_{15}$; $SO_2R_{14}$; $SO_3R_{14}$; $SiR_{16}R_{17}R_{18}$; $OSiR_{16}R_{17}R_{18}$; $POR_{16}R_{17}$; or a radical —X-Sil;
$R_{11}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{22}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_9$; halogen; CN; SH; OH; CHO; $R_{19}$; $OR_{19}$; $SR_{19}$; $C(R_{19})$=$CR_{19}R_{20}$, O—CO—$R_{19}$; $NR_{19}R_{20}$; $CONR_{19}R_{20}$; $SO_2NR_{19}R_{20}$; $SO_2R_{19}$; $COOR_{19}$, $OCOOR_{19}$; $NR_{19}COR_{20}$; $NR_{19}COOR_{20}$; $SiR_{16}R_{17}R_{18}$, $OSiR_{16}R_{17}R_{18}$; P(=O)$R_{16}R_{17}$; or a radical —X-Sil;
$R_{16}$, $R_{17}$ and $R_{18}$ independently form each other are $C_1$-$C_{22}$alkyl; $C_6$-$C_{18}$aryl; or $C_1$-$C_{22}$alkoxy;
$R_{12}$, $R_{13}$, $R_{14}$, $R_{15}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{18}$aryl; $C_3$-$C_{12}$heteroaryl; $C_7$-$C_{20}$aralkyl; or $C_4$-$C_{20}$heteroaralkyl; or $R_{12}$ and $R_{13}$, $R_{14}$ and $R_{15}$, and/or $R_{19}$ and $R_{20}$ may be linked together to form unsubstituted or $C_1$-$C_4$alkyl-substituted pyrrolidine, piperidine, piperazine or morpholine;

X is a linker; and

Sil is a silane-, oligosiloxane or polysiloxane moiety;

if n=1

$R_1$ and $R_2$ independently of each other hydrogen; $C_1$-$C_{22}$ alkyl; $C_2$-$C_{22}$alkenyl; $C_2$-$C_{22}$ alkinyl; $C_3$-$C_{12}$cycloalkyl; $C_3$-$C_{12}$cycloalkenyl; $C_7$-$C_{20}$aralkyl; $C_2$-$C_{20}$heteroalkyl; $C_3$-$C_{12}$cyclo-heteroalkyl; $C_6$-$C_{18}$aryl; $C_4$-$C_{20}$heteroaralkyl; $C_3$-$C_{12}$heteroaryl; —$(CH_2)_u$—$SiR_{16}R_{17}R_{18}$; or —X-Sil;

u is a number from 1 to 12;

$R_3$ is CN; —$COR_7$; —$COOR_7$; or —$CONR_7R_8$;

if n=2 one of $R_1$, $R_2$ and $R_3$ is a bivalent radical; and two of $R_1$, $R_2$ and $R_3$ are defined as for n=1; or $R_1$ and $R_2$ together with the nitrogen atoms form a six-membered heterocyclic ring; and simultaneously $R_3$ is defined as for n=1;

if n=3 one of $R_1$, $R_2$ and $R_3$ is a trivalent radical; and two of $R_1$, $R_2$ and $R_3$ are defined as for n=1;

if n=4 one of $R_1$, $R_2$ and $R_3$ is a tetravalent radical; and two of $R_1$, $R_2$ and $R_3$ are defined as for n=1;

for stabilizing organic UV-sensitive active ingredients.

A BRIEF DESCRIPTION OF THE DRAWINGS

FIG. 1 stabilization of Butyl Methoxydibenzoylmethane (BMDBM) in the presence of the merocyanine compound.

Halogen ist chloro, bromo, fluoro or iodo, preferably chloro.

Alkyl, cycloalkyl, alkenyl, alkylidene or cycloalkenyl may be straight chained or branched, monocyclic or polycyclic.

Alkyl ist for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

Alkenyl is for example straight-chain $C_2$-$C_{12}$alkenyl or preferably branched $C_3$-$C_{12}$alkenyl. $C_1$-$C_{12}$alkyl, like vinyl, allyl, 2-propene-2-yl, 2-butene-1-yl, 3-butene-1-yl, 1,3-butadiene-2-yl, 2-cyclobutene-1-yl, 2-pentene-1-yl, 3-pentene-2-yl, 2-methyl-1-butene-3-yl, 2-methyl-3-butene-2-yl, 3-methyl-2-butene-1-yl, 1,4-pentadiene-3-yl, 2-cyclopentene-1-yl, 2-cyclohexene-1-yl, 3-cyclohexene-1-yl, 2,4-cyclohexadiene-1-yl, 1-p-menthene-8-yl, 4(10)-thujen-10-yl, 2-norbornene-1-yl, 2,5-norbornadiene-1-yl, 7,7-dimethyl-2,4-norcaradiene-3-yl or the different isomers of hexenyl, octenyl, nonenyl, decenyl or dodecenyl.

$C_3$-$C_{12}$cycloalkyl is for example cyclopropyl, cyclobutyl, cyclopentyl, trimethylcyclohexyl or preferably cyclohexyl.

$C_7$-$C_{18}$aralkyl is for example benzyl, 2-benzyl-2-propyl, 6-phenyl-ethyl, 9-fluorenyl, α,α-di-methylbenzyl, ω-phenyl-butyl, ω-phenyl-octyl, ω-phenyl-dodecyl oder 3-methyl-5-(1',1',3',3'-tetramethyl-butyl)-benzyl.

($C_1$-$C_6$)alkylidene is for example methylene, ethyl-1-ene, propyl-2-ene.

$C_6$-$C_{14}$aryl is for example phenyl, naphthyl, biphenylyl, 2-fluorenyl, phenanthryl, anthracenyl or terphenylyl.

$C_3$-$C_{12}$heteroaryl is an unsaturated or aromatic radical having 4n+2 conjugated π-electrons, for example 2-thienyl, 2-furyl, 2-pyridyl, 2-thiazolyl, 2-oxazolyl, 2-imidazolyl, isothiazolyl, tri-azolyl, tetrazolyl or another ring system from thiophene-, furan-, pyridine, thiazol, oxazol, imidazol, isothiazol, triazol, pyridine- and benzene rings, which are unsubstituted or substituted by 1 to 6 ethyl, methyl, ethylene and/or methylene, like benzotriazolyl, bei N-heterocycles optionally in the form of their N-oxides.

$C_4$-$C_{18}$heteroaralkyl is for example $C_1$-$C_8$alkyl substituted with $C_3$-$C_{12}$heteroaryl.

The compounds of formula (1) are preferably present in their E,E-, E,Z- or Z,Z-isomeric forms.

Preferably compounds of formula (1) are used, wherein $L_1$ is hydrogen; or OH;

$R_3$ is $COOR_7$; $COR_7$; —$CONR_7R_8$; or CN;

$L_2$ and $L_3$ independently from each other are hydrogen or $C_1$-$C_{22}$alkyl;

$R_4$ is cyano; $COR_5$, $COOR_5$; $CONR_5R_6$; $C_2$-$C_{12}$heteroalkyl; $C_3$-$C_6$heterocycloalkyl; $C_6$-$C_{18}$aryl; $C_3$-$C_{12}$heteroaryl; $C_2$-$C_{12}$heteroalkyl; or $C_3$-$C_5$heterocycloalkyl;

$R_1$ and $R_2$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_4$-$C_{20}$heteroaralkyl; $C_6$-$C_{18}$aryl; or $C_3$-$C_{12}$heteroaryl; or —X-Sil; or $L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $R_3$ and $R_4$, $R_1$ and $R_2$, $R_5$ and $R_6$, and $R_7$ and $R_8$ may be linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups;

n is 1; and $R_5$, $R_6$, $R_7$ and $R_8$ are defined as in formula (1).

More preferred is the use of the compounds of formula (1), wherein $L_1$ is hydrogen; or OH;

$R_3$ is —$COOR_7$; —$COR_7$; —$CONR_7R_8$; or —CN;

$L_2$ and $L_3$ independently from each other are hydrogen;

$R_4$ is cyano; $COR_5$, $COOR_5$; $CONR_5R_6$;

$R_5$, $R_6$, $R_7$ and $R_8$ are independently of each other hydrogen; $C_1$-$C_{22}$alkyl, $C_2$-$C_{22}$alkenyl, $C_3$-$C_{12}$cycloalkyl; $C_1$-$C_{20}$ heteroalkyl; $C_6$-$C_{18}$ aryl; —$(CH_2)$—$SiR_{16}R_{17}R_{18}$; or a radical —X-Sil; and $R_1$ and $R_2$ independently from each other are hydrogen; $C_1$-$C_{22}$alkyl; or —X-Sil; or $L_1$ and $L_3$, $L_1$ and $R_4$, $L_3$ and $R_1$, $R_3$ and $R_4$, and $R_1$ and $R_2$, may be linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups;

n is 1; and $R_{16}$, $R_{17}$, $R_{18}$, X, Sil and u are defined as in claim 1.

Even more preferred is the use of the compounds of formula (1), wherein $L_1$, $L_2$ and $L_3$ are hydrogen; or $L_1$ and $L_3$ are linked together to form a cyclohexene ring, which may be substituted with one or two methyl groups.

Further preferred are compounds of formula (1), wherein $R_1$ and $R_2$ together form a piperazine ring;

n is 2; and $L_1$, $L_2$, $L_3$, $R_3$ and $R_4$ are defined as in formula (1).

Most preferred merocyanine derivatives used in the present invention are selected from the compounds of formulae (MC 08)
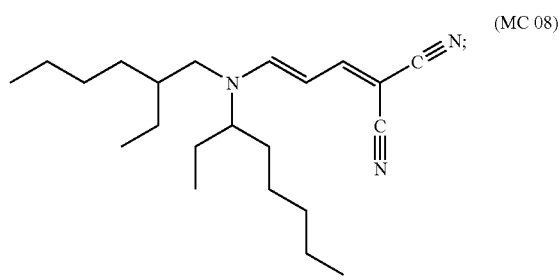
(MC 09)
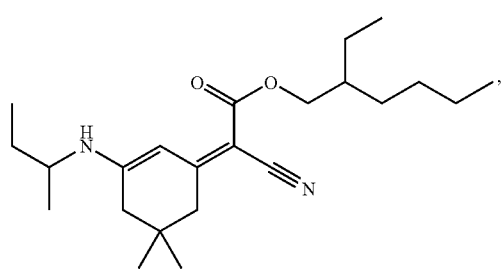
(MC 10)
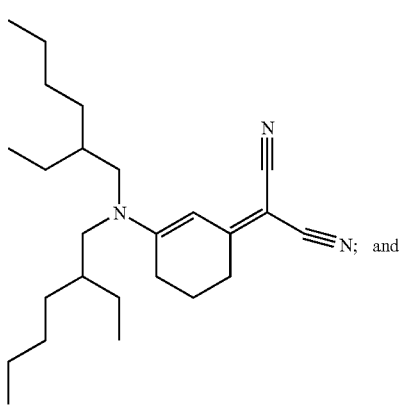
(MC 11)
Specific examples of the merocyanine structure are shown below, but the invention is not limited to these examples.
MC-01
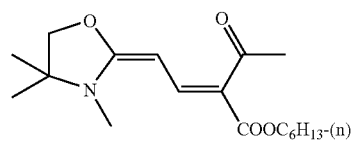
MC-02
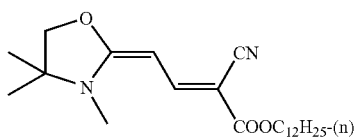
MC-03
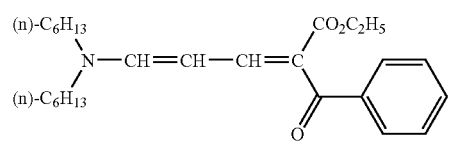
MC-04
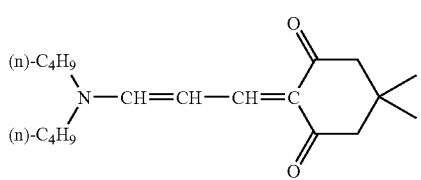
MC-05
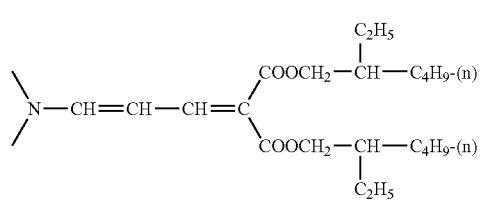
MC-06
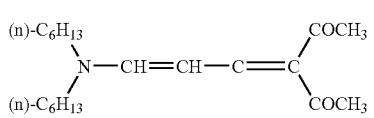

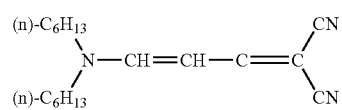
MC-07
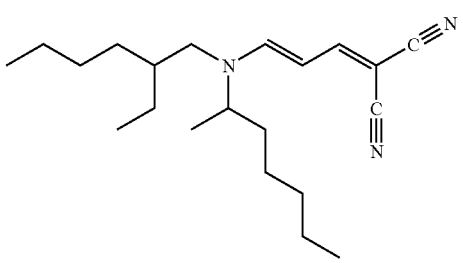
MC-08
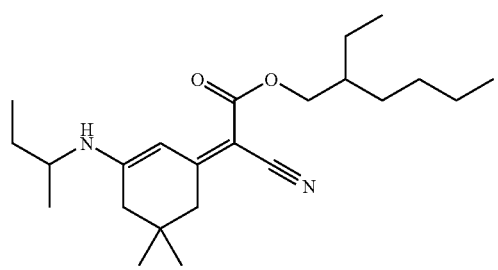
MC-09
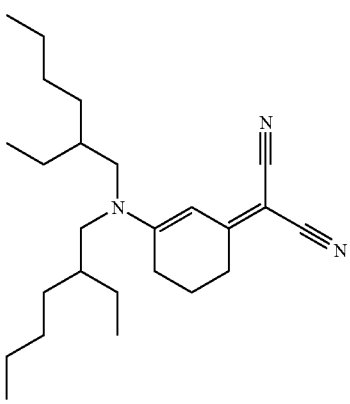
MC-10
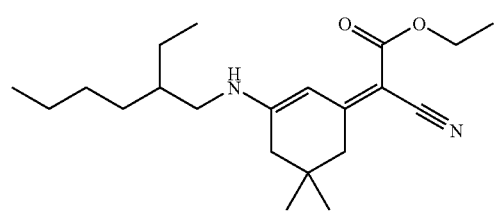
MC-11
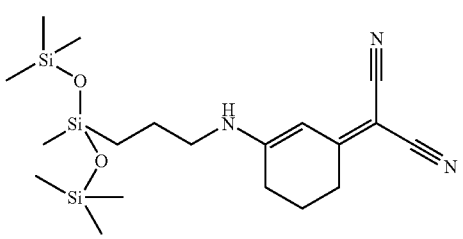
MC-12
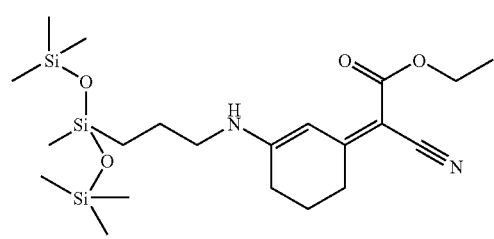
E/Z-isomers
MC-13

MC-14
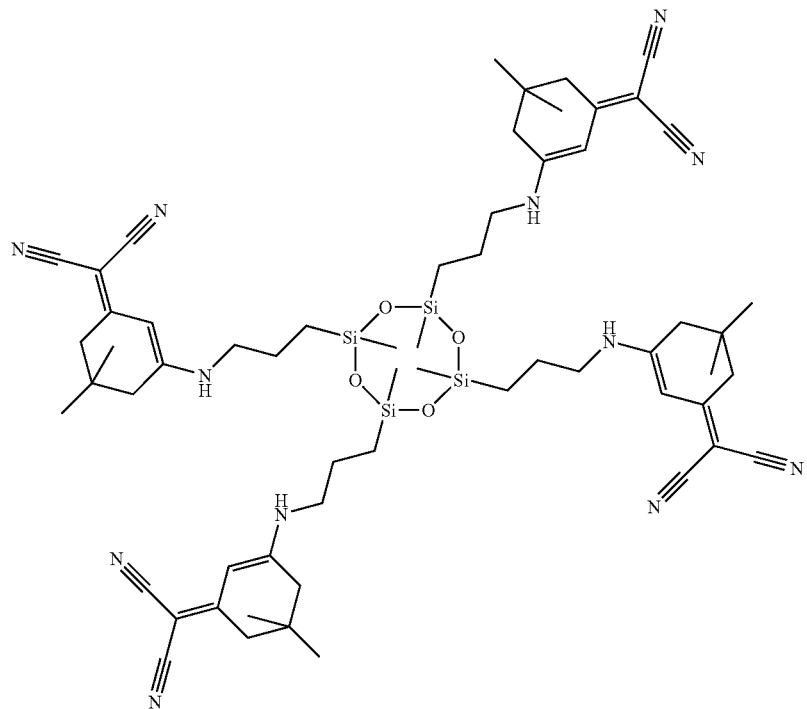
MC-15
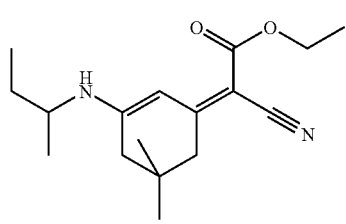
MC-16
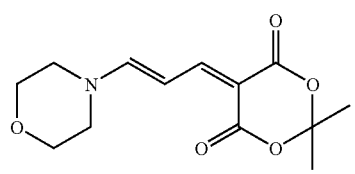
MC-17
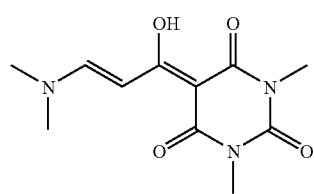
MC-18
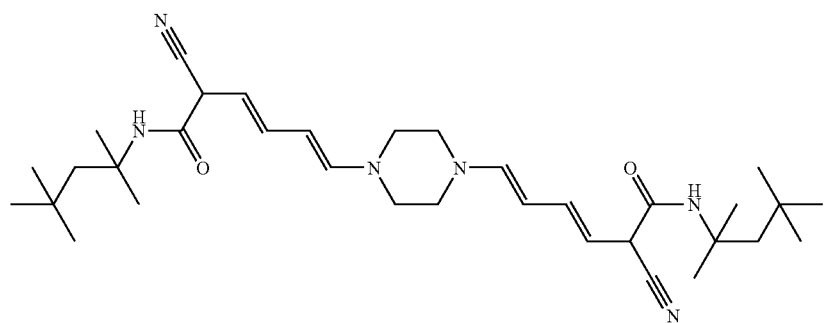

Preferred UV-sensitive active ingredients are organic UV absorbers. Generally, all organic UV absorbers which are commercially available and employed in sunscreen compositions are suitable active ingredients which can be protected by the merocyanine derivatives used in the present invention.

Therefore the present invention refers to a composition comprising at least one screening system in a physiologically acceptable support, characterized in that it comprises:
(a) at least one UV sensitive ingredient; and
(b) at least one merocyanine derivative as defined in any one of the preceding claims.

The UV sensitive derivative or derivatives is (are) present in amounts of 0.01% to 20% by weight, more preferably 0.1% to 10% by weight, still more preferably 0.1% to 5% by weight with respect to the total composition weight.

The merocyanine derivative(s) is (are) present in amounts of 0.01% to 20% by weight, more preferably 0.1% to 10% by weight and still more preferably 0.1% to 5% by weight with respect to the total composition weight.

The composition according to the present invention constitutes a skin care product, a makeup product for the skin, a sun protection product or a skin cleansing product.

Preferably, the composition constitutes a sun protection product.

The merocyanine derivatives of the present invention, present in a composition comprising, in a physiologically acceptable support, at least one UV sensitive ingredient as defined above improve the stability of said UV sensitive ingredient to UV radiation.

Preferably, the organic UV sensitive active ingredients are selected from p-aminobenzoic acid derivatives; salicylic acid derivatives; benzophenone derivatives; dibenzoylmethane derivatives; diphenylacrylates; benzofuran derivatives; polymeric organic UV absorbers; cinnamic acid derivatives; camphor derivatives; hydroxyphenyltriazine derivatives; benzotriazole derivatives; and menthyl o-aminobenzoates.

Examples of the selected UV sensitive active ingredients are listed in Table 1:

TABLE 1

Suible UV sensitive active ingredients which can be stabilized with the UV absorbers according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative; aminohydroxy-benzophenone derivatives disclosed in DE 10011317, EP 1133980 and EP 1046391
dibenzoylmethane derivatives, for example 1-(4-tert-butylphenyl)-3-(4-methoxyphenyl)-propane-1,3-dione;
diphenylacrylates, for example 2-ethylhexyl 2-cyano-3,3-diphenylacrylate, and 3-(benzofuranyl) 2-cyanoacrylate;
benzofuran derivatives, especially 2-(p-aminophenyl)benzofuran derivatives, described in EP-A-582 189, US-A-5 338 539, US-A-5 518 713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in US-A-5 601 811 and WO 97/00851;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine; trianilino-s-triazine derivatives, for example 2,4,6-trianiline-(p-carbo-2'-ethyl-1'-oxy)-1,3,5-triazine and the UV absorbers disclosed in US-A-5 332 568, EP-A-517 104, EP-A-507 691, WO 93/17002 and EP-A-570 838;
benzotriazole compounds, for example 2,2'-methylene-bis(6-(2H-benzotriazol-2-yl)-4-(1,1,3,3-tetramethylbutyl)-phenol;

Furthermore, the UV absorbers listed in the references given in Table 3 may be stabilized by the merocynine derivatives according to present invention:

TABLE 2

Suitable UV filter substances which can be additionally used with the UV absorbers according to the present invention

| DE 10013318 | T 1 pp 8-9, all Examples pp 10-13, T 2 pp 13-14, all Examples p 14, Ex A, B, C, D, E, F pp 19-20 |
|---|---|
| DE102004038485A1 | Formula 1 on p 2; Ex 1-4 on p 13; |

TABLE 2-continued

Suitable UV filter substances which can be additionally used with the UV absorbers according to the present invention

| | |
|---|---|
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp 18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |

TABLE 2-continued

Suitable UV filter substances which can be additionally used with the UV absorbers according to the present invention

| | |
|---|---|
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| US 6 800 274 B2 | Formulas I-VI and IX-XII on pp 14-18; |
| US 6 890 520 B2 | Ex 1-10 on pp 6-9; |
| US 6926887 B2 | Ex A on pp5/6; Formulas I-VIII on pp 27-29; |
| US 6936735 B2 | Formulas 1-2 on p 2; formula 3-4 on p 6; |
| US 6962692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

Preferably, the organic UV absorber stabilized by the merocanine derivatives according to the present invention is selected from a dibenzoylmethane derivative, and most preferably it is 4-(tert-butyl)-4'-methoxydibenzoylmethane.

In a very preferred embodiment of the present invention the merocyanine derivative of formula (MC 11) is used for the stabilization of 4-(tert-butyl)-4'-methoxydibenzoylmethane.

The UV-sensitive active ingredients present in a cosmetic or dermatological formulation are highly protected against UV induced degradation. This is valid in particular for dibenzoyl-methane derivatives. By stabilizing UV sensitive UV absorbers like avobenzone with a merocyanine derivative according to the present invention photostable sunscreen formulations are obtained.

Examples of photostable sun screen formulation according to the present invention are listed below:

| Example 1.1: O/W-Emulsion | % b.w. | % b.w. | % b.w. | % b.w. |
|---|---|---|---|---|
| Sorbitan Stearate | 3.00 | 3.00 | 3.00 | 3.00 |
| Polyglyceryl-3 Methylglucose Distearate | 1.50 | 1.50 | 1.50 | 1.50 |

-continued

| Example 1.1: O/W-Emulsion | % b.w. | % b.w. | % b.w. | % b.w. |
|---|---|---|---|---|
| Octyldodecanol | 10.00 | 10.00 | 10.00 | 10.00 |
| Dicaprylyl Ether | 5.00 | 5.00 | 5.00 | 5.00 |
| Mineral Oil | 5.00 | 5.00 | 5.00 | 5.00 |
| *Ricinus* Oil | 2.00 | 2.00 | 2.00 | 2.00 |
| Butylene Glycol Dicaprylate/Dicaprate | 5.00 | 5.00 | 5.00 | 5.00 |
| Vitamin-E Acetate | 0.50 | 0.50 | 0.50 | 0.50 |
| Octyltriazone | 4.00 | 4.00 | 4.00 | 4.00 |
| Octocrylene | 8.00 | 8.00 | 8.00 | 8.00 |
| 4-Methylbenzylidene Camphor | 4.00 | 4.00 | 4.00 | 4.00 |
| Butyl Methoxydibenzoylmethane | 3.00 | 3.00 | 3.00 | 3.00 |
| α-Glucosylrutin | 1.00 | 1.00 | 1.00 | 1.00 |
| Boron Nitride | 2.00 | 2.00 | 2.00 | 2.00 |
| Preservative | 0.50 | 0.50 | 0.50 | 0.50 |
| Glycerin | 10.00 | 10.00 | 10.00 | 10.00 |
| Merocyanine of formula MC-08 | 1.50 | | | |
| Merocyanine of formula MC-09 | | 1.50 | | |
| Merocyanine of formula MC-10 | | | 1.50 | |
| Merocyanine of formula MC-11 | | | | 1.50 |
| Xanthan Gum | 0.20 | 0.20 | 0.20 | 0.20 |
| Permulen TR1 | 0.10 | 0.10 | 0.10 | 0.10 |
| Phenylbenzimidazole Sulfonic Acid | 2.00 | 2.00 | 2.00 | 2.00 |
| NaOH 45% | 1.20 | 1.20 | 1.20 | 1.20 |
| Water | ad 100.00 | ad 100.00 | ad 100.00 | ad 100.00 |

| Example 1.2: W/O-Emulsion | | | | |
|---|---|---|---|---|
| | % b.w. | % b.w. | % b.w. | % b.w. |
| Polyglyceryl-2-dipolyhydroxy-stearate | 5.00 | 5.00 | 5.00 | 5.00 |
| Dimethicone | 2.00 | 2.00 | 2.00 | 2.00 |
| Mineral Oil | 5.00 | 5.00 | 5.00 | 5.00 |
| Isohexadecane | 5.00 | 5.00 | 5.00 | 5.00 |
| Butylene Glycol Dicaprylate/Dicaprate | 10;00 | 10;00 | 10;00 | 10;00 |
| $C_{12-15}$ Alkylbenzoate | 7.00 | 7.00 | 7.00 | 7.00 |
| Dioctyl Butamido Triazone | 3.00 | 3.00 | 3.00 | 3.00 |
| 4-Methylbenzylidene Camphor | 2.00 | 2.00 | 2.00 | 2.00 |
| Butyl Methoxydibenzoylmethane | 2.00 | 2.00 | 2.00 | 2.00 |
| Titanium Dioxide | 4.00 | 4.00 | 4.00 | 4.00 |
| α-Glucosylrutin | 0.50 | 0:50 | 0.50 | 0.50 |
| Preservative | 0.50 | 0.50 | 0.50 | 0.50 |
| Glycerin | 5.00 | 5.00 | 5.00 | 5.00 |
| Merocyanine of formula MC-08 | 4.50 | | | |
| Merocyanine of formula MC-09 | | 4.50 | | |
| Merocyanine of formula MC-10 | | | 4.50 | |
| Merocyanine of formula MC-11 | | | | 4.50 |
| $MgSO_4$ | 1.00 | 1.00 | 1.00 | 1.00 |
| Water | ad 100.00 | ad 100.00 | ad 100.00 | ad 100.00 |

| Example 1.3: Hydrodispersion | | | | |
|---|---|---|---|---|
| | % b.w. | % b.w. | % b.w. | % b.w. |
| Caprylic Acid/Capric Acid Triglyceride | 10.00 | 10.00 | 10.00 | 10.00 |
| Cetyldodecanol | 5.00 | 5.00 | 5.00 | 5.00 |
| Dicaprylyl Ether | 2.00 | 2.00 | 2.00 | 2.00 |
| Dimethicone | 1.00 | 1.00 | 1.00 | 1.00 |
| Vitamin-E Acetate | 0.50 | 0.50 | 0.50 | 0.50 |
| Octyltriazone | 2.00 | 2.00 | 2.00 | 2.00 |
| 4-Methylbenzylidene Camphor | 4.00 | 4.00 | 4.00 | 4.00 |
| Butyl Methoxydibenzoylmethane | 2.00 | 2.00 | 2.00 | 2.00 |
| Titanium Dioxide | 1.00 | 1.00 | 1.00 | 1.00 |
| α-Glucosylrutin | 0.75 | 0.75 | 0.75 | 0.75 |
| Preservative | 0:50 | 0:50 | 0:50 | 0:50 |
| Glycerin | 3.00 | 3.00 | 3.00 | 3.00 |
| Merocyanine of formula MC-08 | 2.20 | | | |
| Merocyanine of formula MC-09 | | 2.20 | | |
| Merocyanine of formula MC-10 | | | 2.20 | |
| Merocyanine of formula MC-11 | | | | 2.20 |
| Xanthan Gum | 0.40 | 0.40 | 0.40 | 0.40 |
| Crosslinked Acrylic Acid/($C_{10-30}$) Alkyl Acrylate Copolymer copolymer | 0.40 | 0.40 | 0.40 | 0.40 |
| Water | ad 100.00 | ad 100.00 | ad 100.00 | ad 100.00 |

| Example 2.1: O/W Emulsion | | | | |
|---|---|---|---|---|
| | % b.w. | % b.w. | % b.w. | % b.w. |
| Stearic Acid | 1.50 | 1.50 | 1.50 | 1.50 |
| Glycerin Monostearate | 3.00 | 3.00 | 3.00 | 3.00 |
| Caprylic Acid/Capric Acid Triglyceride | 10.00 | 10.00 | 10.00 | 10.00 |
| Dicaprylyl Ether | 5.00 | 5.00 | 5.00 | 5.00 |
| Hydrated Polyisobutene | 2.00 | 2.00 | 2.00 | 2.00 |
| Vitamin-E Acetate | 0.50 | 0.50 | 0.50 | 0.50 |
| Octyltriazone | 2.00 | 2.00 | 2.00 | 2.00 |
| Dioctyl Butamido Triazone | 2.00 | 2.00 | 2.00 | 2.00 |
| Butyl Methoxydibenzoylmethane | 2.00 | 2.00 | 2.00 | 2.00 |
| Titanium Dioxide | 1.00 | 1.00 | 1.00 | 1.00 |
| $C_{18-36}$ Triglyceride | 5.00 | 5.00 | 5.00 | 5.00 |
| Merocyanine of formula MC-08 | 5.80 | | | |
| Merocyanine of formula MC-09 | | 5.80 | | |
| Merocyanine of formula MC-10 | | | 5.80 | |
| Merocyanine of formula MC-11 | | | | 5.80 |
| Xanthan Gum | 0.30 | 0.30 | 0.30 | 0.50 |
| NaOH 45% | 0.50 | 0.50 | 0.50 | q.s. |
| Preservative, Perfume, Dyes | q.s. | q.s. | q.s. | q.s. |
| Water | ad 100.00 | ad 100.00 | ad 100.00 | ad 100.00 |

| Example 2.2: Oil Gel | | | | |
|---|---|---|---|---|
| | % b.w. | % b.w. | % b.w. | % b.w. |
| Caprylic Acid/Capric Acid Triglyceride | 5.00 | 5.00 | 5.00 | 5.00 |
| Dicaprylyl Ether | 5.00 | 5.00 | 5.00 | 5.00 |
| Dimethicone | 5.00 | 5.00 | 5.00 | 5.00 |
| Mineral Oil | 30.00 | 30.00 | 30.00 | 30.00 |
| Isohexadecane | 10.00 | 10.00 | 10.00 | 10.00 |
| Hydrated Polyisobutene | 20.00 | 20.00 | 20.00 | 20.00 |
| Butylene Glycol Dicaprylate/Dicaprate | 5.00 | 5.00 | 5.00 | 5.00 |
| $C_{12-15}$ Alkylbenzoate | 5.00 | 5.00 | 5.00 | 5.00 |
| Vitamin-E Acetate | 0.50 | 0.50 | 0.50 | 0.50 |
| Octyltriazone | 2.00 | 2.00 | 2.00 | 2.00 |
| Butyl Methoxydibenzoylmethane | 1.00 | 1.00 | 1.00 | 1.00 |
| Aerosil R 972 | 1.00 | 1.00 | 1.00 | 1.00 |
| $C_{18-38}$ Triglyceride | 10.00 | 10.00 | 10.00 | 10.00 |
| Merocyanine of formula MC-08 | 0.50 | | | |
| Merocyanine of formula MC-09 | | 0.50 | | |
| Merocyanine of formula MC-10 | | | 0.50 | |
| Merocyanine of formula MC-11 | | | | 0.50. |
| Preservative, Parfurne, Dyes, Water | q.s. | q.s. | q.s. | q.s |

| Example 3.1: O/W Emulsion | | | | |
|---|---|---|---|---|
| | % b.w. | % b.w. | % b.w. | % b.w. |
| Sorbitan Stearate | 3.00 | 3.00 | 3.00 | 3.00 |
| Polyglyceryl-3 Methylglucose Distearate | 1.50 | 1.50 | 1.50 | 1.50 |
| Octyldodecanol | 10.00 | 10.00 | 10.00 | 10.00 |
| Dicaprylyl Ether | 5.00 | 5.00 | 5.00 | 5.00 |
| Mineral Oil | 5.00 | 5.00 | 5.00 | 5.00 |
| Castor Oil | 2.00 | 2.00 | 2.00 | 2.00 |
| Butylene Glycol Dicaprylate/Dicaprate | 5.00 | 5.00 | 5.00 | 5.00 |
| Vitamin E Acetate | 0.50 | 0.50 | 0.50 | 0.50 |
| Octocrylene | 8.00 | 8.00 | 8.00 | 8.00 |
| Bis-Ethylhexyloxyphenol Methoxyphenyl Triazine (Tinosorb S) | 1.50 | 1.50 | 1.50 | 1.50 |
| Octyltriazone | 4.00 | 4.00 | 4.00 | 4.00 |
| 4-Methylbenzylidene Camphor | 3.00 | 3.00 | 3.00 | 3.00 |
| Butyl Methoxydibenzoylmethane | 4.00 | 4.00 | 4.00 | 4.00 |
| Preservative | q.s. | q.s. | q.s. | q.s. |
| Glycerol | 10.00 | 10.00 | 10.00 | 10.00 |
| Merocyanine of formula MC-08 | 8.00 | | | |
| Merocyanine of formula MC-09 | | 8.00 | | |
| Merocyanine of formula MC-10 | | | 8.00 | |
| Merocyanine of formula MC-11 | | | | 8.00 |
| Xanthan Gum | 0.20 | 0.20 | 0.20 | 0.20 |
| Acrylates/C10-30 Alkyl Acrylate Crosspolymer (Pemulen TR1) | 2.00 | 2.00 | 2.00 | 2.00 |
| Phenylbenzimidazole Sulfonic Acid | 0.10 | 0.10 | 0.10 | 0.10 |

Example 3.1: O/W Emulsion

|  | % b.w. | % b.w. | % b.w. | % b.w. |
|---|---|---|---|---|
| NaOH 45% | 1.20 | 1.20 | 1.20 | 1.20 |
| Water | ad 100.00 | ad 100.00 | ad 100.00 | ad 100.00 |

Example 3.2: W/O Emulsion

|  | % b.w. | % b.w. | % b.w. | % b.w. |
|---|---|---|---|---|
| Cetyldimethicone Copolyol | 5.00 | 5.00 | 5.00 | 5.00 |
| Dimethicone | 5.00 | 5.00 | 5.00 | 5.00 |
| Mineral Oil | 2.00 | 2.00 | 2.00 | 2.00 |
| Isohexadecane | 2.00 | 2.00 | 2.00 | 2.00 |
| $C_{12-15}$ Alkylbenzoate | 5.00 | 5.00 | 5.00 | 5.00 |
| Octocrylene | 15.00 | 15.00 | 15.00 | 15.00 |
| Bis-Ethylhexyloxyphenol Methoxyphenyl Triazine (Tinosorb S) | 6.00 | 6.00 | 6.00 | 6.00 |
| 4-Methylbenzylidene Camphor | 4.00 | 4.00 | 4.00 | 4.00 |
| Butyl Methoxydibenzoylmethane | 2.00 | 2.00 | 2.00 | 2.00 |
| Titanium Dioxide | 2.00 | 2.00 | 2.00 | 2.00 |
| Preservative | q.s. | q.s. | q.s. | q.s. |
| Glycerol | 5.00 | 5.00 | 5.00 | 5.00 |
| Merocyanine of formula MC-08 | 1.30 |  |  |  |
| Merocyanine of formula MC-09 |  | 1.30 |  |  |
| Merocyanine of formula MC-10 |  |  | 1.30 |  |
| Merocyanine of formula MC-11 |  |  |  | 1.30 |
| NaCl | 1.00 | 1.00 | 1.00 | 1.00 |
| Phenylbenzimidazole Sulfonic Acid | 4.00 | 4.00 | 4.00 | 4.00 |
| NaOH 45% | 1.30 | 1.30 | 1.30 | 1.30 |
| Water | ad 100.00 | ad 100.00 | ad 100.00 | ad 100.00 |

Example 3.3: Hydrodispersion

|  | % b.w. | % b.w. | % b.w. | % b.w. |
|---|---|---|---|---|
| Caprylic Acid/Capric Acid Triglyceride | 10.00 | 10.00 | 10.00 | 10.00 |
| Octyldodecanol | 5.00 | 5.00 | 5.00 | 5.00 |
| Dicaprylyl Ether | 2.00 | 2.00 | 2.00 | 2.00 |
| Dimethicone | 1.00 | 1.00 | 1.00 | 1.00 |
| Vitamin E Acetate | 0.50 | 0.50 | 0.50 | 0.50 |
| Octyltriazone | 2.00 | 2.00 | 2.00 | 2.00 |
| 4-Methylbenzylidene Camphor | 4.00 | 4.00 | 4.00 | 4.00 |
| Butyl Methoxydibenzoylmethane | 2.00 | 2.00 | 2.00 | 2.00 |
| Titanium Dioxide | 1.00 | 1.00 | 1.00 | 1.00 |
| Preservative | q.s. | q.s. | q.s. | q.s. |
| Glycerol | 3.00 | 3.00 | 3.00 | 3.00 |
| Merocyanine of formula MC-08 | 0.90 |  |  |  |
| Merocyanine of formula MC-09 |  | 0.90 |  |  |
| Merocyanine of formula MC-10 |  |  | 0.90 |  |
| Merocyanine of formula MC-11 |  |  |  | 0.90 |
| Xanthan Gum | 0.40 | 0.40 | 0.40 | 0.40 |
| Acrylates/C10-30 Alkyl Acrylate Crosspolymer (Pemulen TR1) | 0.40 | 0.40 | 0.40 | 0.40 |
| NaOH 45% | 0.40 | 0.40 | 0.40 | 0.40 |
| Water | ad 100.00 | ad 100.00 | ad 100.00 | ad 100.00 |

| Examples 4.1-4.8: Sun Milk | | | | | | | | |
|---|---|---|---|---|---|---|---|---|
| | 4.1 | 4.2 | 4.3 | 4.4 | 4.5 | 4.6 | 4.7 | 4.8 |
| Butyl Methoxydibenzoylmethane | 1.0 | 1.0 | 1.0 | 1.0 | 1.0 | 1.0 | 1.0 | 1.0 |
| Octocrylene | 7.5 | 7.5 | 7.5 | 7.5 | 7.5 | 7.5 | 7.5 | 7.5 |
| Isohexadecane | 3.0 | 3.0 | 3.0 | 3.0 | 3.0 | 3.0 | 3.0 | 3.0 |
| Cyclopentasiloxane | 4.0 | 4.0 | 4.0 | 4.0 | 4.0 | 4.0 | 4.0 | 4.0 |
| Terephthalylidene Dicamphor Sulfonic Acid | 0.3 | 0.3 | 0.3 | 0.3 | 0.3 | 0.3 | 0.3 | 0.3 |
| Titanium Dioxide Particles size 10 to 100 nm | 1.7 | 1.7 | 1.7 | 1.7 | 1.7 | 1.7 | 1.7 | 1.7 |
| TiO2 (and) isodeceth-6(and)Oleth-10(and)Alumina(and) Simethicone | | 1.5 | | 1.5 | | 1.5 | | 1.5 |
| TiO2(and)isolaureth-4 Phosphate(and)Vinylbuteth-25/Sodium maleate copolymer | 0.5 | 0.5 | 0.5 | 0.5 | 0.5 | 0.5 | 0.5 | 0.5 |
| TiO2(and)Diethylhexylcarbonate(and) polyglyceryl-6 polyhydroxystearate | 0.8 | 0.8 | 0.8 | 0.8 | 0.8 | 0.8 | 0.8 | 0.8 |
| TiO2(and)Aluminum hydroxide(and)Dimethiconol methicone copolymer | | 3.0 | | 3.0 | | 3.0 | | 3.0 |
| ZnO particles size 10 to 100 nm | 3.0 | 3.0 | 3.0 | 3.0 | 3.0 | 3.0 | 3.0 | 3.0 |
| Pentaerythrityl Distearate | | 1.5 | | 1.5 | | 1.5 | | 1.5 |
| Stearic acid | 0.5 | 0.5 | 0.5 | 0.5 | 0.5 | 0.5 | 0.5 | 0.5 |
| PEG-100 Stearate (and) Glyceryl Stearate | 0.8 | 0.8 | 0.8 | 0.8 | 0.8 | 0.8 | 0.8 | 0.8 |
| Octadecene/MA Copolymer (and) Methyl Acetyl Ricinoleate (and) Di-methylhepthyl Adipate | | 3.0 | | 3.0 | | 3.0 | | 3.0 |
| C20-22 Alkyl Phosphate (and) C20-22 Alcohols | | 2.5 | | 2.5 | | 2.5 | | 2.5 |
| Potassium Cetyl Phosphate | 1.3 | | 1.3 | | 1.3 | | 1.3 | |
| PVP/Eicosene Copolymer | 1.0 | | 1.0 | | 1.0 | | 1.0 | |
| Aqua | Qs to 100 | Qs to 100 | Qs to 100 | Qs to 100 | Qs to 100 | Qs to 100 | Qs to 100 | Qs to 100 |
| Merocyanine of formula MC-08 | 0.90 | | | | | | | |
| Merocyanine of formula MC-08 | | 1.00 | | | | | | |
| Merocyanine of formula MC-09 | | | 0.90 | | | | | |
| Merocyanine of formula MC-09 | | | | 1.00 | | | | |
| Merocyanine of formula MC-10 | | | | | 0.90 | | | |
| Merocyanine of formula MC-10 | | | | | | 1.00 | | |
| Merocyanine of formula MC-11 | | | | | | | 0.90 | |
| Merocyanine of formula MC-11 | | | | | | | | 1.00 |
| Glycerin | 4.0 | 9.0 | 4.0 | 9.0 | 9.0 | 9.0 | 9.0 | 9.0 |
| Propylene Glycol | 5.0 | 5.0 | 5.0 | 5.0 | 5.0 | 5.0 | 5.0 | 5.0 |
| Xanthan Gum | 0.2 | 0.2 | 0.2 | 0.2 | 0.2 | 0.2 | 0.2 | 0.2 |
| Disteareth-75 IPDI | | 0.3 | | 0.3 | | 0.3 | | 0.3 |
| Acrylates/C10-30 Alkyl Acrylate Crosspolymer | 0.2 | | 0.2 | | 0.2 | | 0.2 | |
| Disodium EDTA | 0.2 | 0.2 | 0.2 | 0.2 | 0.2 | 0.2 | 0.2 | 0.2 |
| Triethanolamine | qs | qs | qs | qs | qs | qs | qs | qs |
| Dimethicone | 0.4 | 0.4 | 0.4 | 0.4 | 0.4 | 0.4 | 0.4 | 0.4 |
| Phenoxyethanol (and) Methylparaben (and) Ethylparaben (and) Butylparaben (and) Propylparaben (and) Isobutylparaben | 0.7 | 0.7 | 0.7 | 0.7 | 0.7 | 0.7 | 0.7 | 0.7 |
| Tocopheryl Acetate | 0.9 | 0.9 | 0.9 | 0.9 | 0.9 | 0.9 | 0.9 | 0.9 |

| Example 5.1: O/W-Lotion | | | | |
|---|---|---|---|---|
| | % b.w. | % b.w. | % b.w. | % b.w. |
| Glycerylstearate SE | 3.50 | 3.50 | 3.50 | 3.50 |
| Stearic Acid | 1.80 | 1.80 | 1.80 | 1.80 |
| Glycerin | 3.00 | 3.00 | 3.00 | 3.00 |
| Celylstearylalcohol | 0.50 | 0.50 | 0.50 | 0.50 |
| Octyidodecanol | 7.00 | 7.00 | 7.00 | 7.00 |
| Dicaprylyl Ether | 8.00 | 8.00 | 8.00 | 8.00 |
| 4,4',4''-(1.3,5-Triazine-2,4,6-triyltriimino)-tris-benzoic acid tris(2-ethylhexylester) | 3.00 | 3.00 | 3.00 | 3.00 |
| Butyl Methoxydibenzoylmethane | 2.00 | 2.00 | 2.00 | 2.00 |
| Methylbenzylidencamphor | 1.04 | 1.04 | 1.04 | 1.04 |
| Titanium Dioxide | 2.00 | 2.00 | 2.00 | 2.00 |
| Mixed Iron Oxides | 1.00 | 1.00 | 1.00 | 1.00 |
| Merocyanine of formula MC-08 | 1.40 | | | |

-continued

| Example 5.1: O/W-Lotion | | | | |
|---|---|---|---|---|
| | % b.w. | % b.w. | % b.w. | % b.w. |
| Merocyanine of formula MC-09 | | 1.40 | | |
| Merocyanine of formula MC-10 | | | 1.40 | |
| Merocyanine of formula MC-11 | | | | 1.40 |
| Carbomer | 0.20 | 0.20 | 0.20 | 0.20 |
| NaOH 45% | 0.20 | 0.20 | 0.20 | 0.20 |
| Preservative | q.s. | q.s. | q.s. | q.s. |
| Parfum | q.s. | q.s. | q.s. | q.s. |
| Aqua | ad 100.00 | ad 100.00 | ad 100.00 | ad 100.00 |

| Example 5.2: Emulsifier-free Sunscreen Lotion SPF 30 | | | | |
|---|---|---|---|---|
| | % b.w. | % b.w. | % b.w. | % b.w. |
| Caprylic Acid/Capric Acid Triglyceride | 30.00 | 30.00 | 30.00 | 30.00 |
| 4,4',4"-(1.3,5-Triazine-2,4,6-triyltriimino)-tris-benzoic acid tris(2-ethylhexylester) | 4.00 | 4.00 | 4.00 | 4.00 |
| 4-Methylbenzylidene Camphor | 2.00 | 2.00 | 2.00 | 2.00 |
| Ethylhexyl Salicylate | 6.00 | 6.00 | 6.00 | 6.00 |
| Butyl Methoxydibenzoylmethane | 2.00 | 2.00 | 2.00 | 2.00 |
| Titanium Dioxideand Aluminaand Simethicone (Eusolex T2000) | 4.00 | 4.00 | 4.00 | 4.00 |
| Aerosil R 972 | 2.00 | 2.00 | 2.00 | 2.00 |
| Lecithin | 5.00 | 5.00 | 5.00 | 5.00 |
| Merocyanine of formula MC-08 | 1.80 | | | |
| Merocyanine of formula MC-09 | | 1.80 | | |
| Merocyanine of formula MC-10 | | | 1.80 | |
| Merocyanine of formula MC-11 | | | | 1.80 |
| Stannous Oxide | 2.50 | 2.50 | 2.50 | 2.50 |
| Cetylhydroxyethylcellulose | 0.50 | 0.50 | 0.50 | 0.50 |
| Glycerin | 10.00 | 10.00 | 10.00 | 10.00 |
| Water | ad 100.00 | ad 100.00 | ad 100.00 | ad 100.00 |

| Example 5.3: O/W-Lotion | | | | |
|---|---|---|---|---|
| | % b.w. | % b.w. | % b.w. | % b.w. |
| Glycerylstearate SE | 3.50 | 3.50 | 3.50 | 3.50 |
| Stearic Acid | 1.80 | 1.80 | 1.80 | 1.80 |
| Glycerin | 3.00 | 3.00 | 3.00 | 3.00 |
| Celylstearylalcohol | 0.50 | 0.50 | 0.50 | 0.50 |
| Octyisodecanol | 7.00 | 7.00 | 7.00 | 7.00 |
| Dicaprylyl Ether | 8.00 | 8.00 | 8.00 | 8.00 |
| 4,4',4"-(1.3,5-Triazine-2,4,6-triyltriimino)-tris-benzoic acid tris(2-ethylhexylester) | 3.00 | 3.00 | 3.00 | 3.00 |
| Butyl Methoxydibenzoylmethane | 2.00 | 2.00 | 2.00 | 2.00 |
| 4-Methylbenzylidene Camphor | 1.00 | 1.00 | 1.00 | 1.00 |
| Titanium Dioxide | 2.00 | 2.00 | 2.00 | 2.00 |
| Mixed Iron Oxides | 1.00 | 1.00 | 1.00 | 1.00 |
| Carbomer | 0.20 | 0.20 | 0.20 | 0.20 |
| Merocyanine of formula MC-08 | 1.50 | | | |
| Merocyanine of formula MC-09 | | 1.50 | | |
| Merocyanine of formula MC-10 | | | 1.50 | |
| Merocyanine of formula MC-11 | | | | 1.50 |
| NaOH 45% | 0.20 | 0.20 | 0.20 | 0.20 |
| Preservative | q.s. | q.s. | q.s. | q.s. |
| Parfum | q.s. | q.s. | q.s. | q.s. |
| Aqua | ad 100.00 | ad 100.00 | ad 100.00 | ad 100.00 |

| Example 5.5: O/W Creme | | | | |
|---|---|---|---|---|
| | % b.w. | % b.w. | % b.w. | % b.w. |
| Glycerylstearate SE | 3.50 | 3.50 | 3.50 | 3.50 |
| Stearic Acid | 3.50 | 3.50 | 3.50 | 3.50 |
| Butylene Gglycol | 5.00 | 5.00 | 5.00 | 5.00 |
| Cetylstearylalcohol | 3.00 | 3.00 | 3.00 | 3.00 |
| $C_{12-15}$ Alkylbenzoate | 10.00 | 10.00 | 10.00 | 10.00 |
| Ethylhexyl Triazone | 4.00 | 4.00 | 4.00 | 4.00 |
| Butyl Methoxydibenzoylmethane | 2.00 | 2.00 | 2.00 | 2.00 |
| 4-Methylbenzylidene Camphor | 1.00 | 1.00 | 1.00 | 1.00 |
| Lecithin | 3.00 | 3.00 | 3.00 | 3.00 |
| Merocyanine of formula MC-08 | 1.80 | | | |
| Merocyanine of formula MC-09 | | 1.80 | | |
| Merocyanine of formula MC-10 | | | 1.80 | |
| Merocyanine of formula MC-11 | | | | 1.80 |
| Carbomer | 0.20 | 0.20 | 0.20 | 0.20 |
| NaOH 45% | 0.35 | 0.35 | 0.35 | 0.35 |
| Preservative | q.s. | q.s. | q.s. | q.s. |
| Perfume | q.s. | q.s. | q.s. | q.s. |
| Water, demin. | ad 100.00 | ad 100.00 | ad 100.00 | ad 100.00 |

| Example 5.6: W/O-Lotion | | | | |
|---|---|---|---|---|
| | % b.w. | % b.w. | % b.w. | % b.w. |
| Polyglyceryl-2-Polyhydroxy-stearate | 3.50 | 3.50 | 3.50 | 3.50 |
| Polyglyceryl-3-Diisostearate | 3.50 | 3.50 | 3.50 | 3.50 |
| Butylene Glycol | 5.00 | 5.00 | 5.00 | 5.00 |
| Ceresin | 3.00 | 3.00 | 3.00 | 3.00 |
| $C_{12-15}$ Alkylbenzoate | 10.00 | 10.00 | 10.00 | 10.00 |
| Triazine | 4.00 | 4.00 | 4.00 | 4.00 |
| Lecithin | 2.00 | 2.00 | 2.00 | 2.00 |
| Butyl Methoxydibenzoylmethane | 2.00 | 2.00 | 2.00 | 2.00 |
| 4-Methylbenzylidene Camphor | 1.00 | 1.00 | 1.00 | 1.00 |
| Titanium Dioxide | 2.00 | 2.00 | 2.00 | 2.00 |
| Merocyanine of formula MC-08 | 1.30 | | | |
| Merocyanine of formula MC-09 | | 1.30 | | |
| Merocyanine of formula MC-10 | | | 1.30 | |
| Merocyanine of formula MC-11 | | | | 1.30 |
| Vaseline | 2.00 | 2.00 | 2.00 | 2.00 |
| NaOH (45% ig) | 0.35 | 0.35 | 0.35 | 0.35 |
| Preservative | q.s. | q.s. | q.s. | q.s. |
| Parfume | q.s. | q.s. | q.s. | q.s. |
| Water | ad 100 | ad 100 | ad 100 | ad 100 |

| Examples 6.1-6.8 | | | | | | | | |
|---|---|---|---|---|---|---|---|---|
| | 6.1 Hydro dispersion | 6.2 Spray | 6.3 Hydro dispersion | 6.4 Spray | 6.5 Hydro dispersion | 6.6 Spray | 6.7 Hydro dispersion | 6.8 Spray |
| Glycerin Monostearate | 1.0 | | 1.0 | | 1.0 | | 1.0 | |
| Glycerin Monostearate SE | | 4.50 | | 4.50 | | 4.50 | | 4.50 |
| Ceteareth-20 | | 1.00 | | 1.00 | | 1.00 | | 1.00 |
| Dimethicone | | 2.00 | | 2.00 | | 2.00 | | 2.00 |
| Phenyl Trimethicone | 1 | | 1 | | 1 | | 1 | |
| Vitamin E-Acetate | 0.9 | 0.9 | 0.9 | 0.9 | 0.9 | 0.9 | 0.9 | 0.9 |
| Caprylic Acid/Capric Acid Triglyceride | 3 | | 3 | | 3 | | 3 | |
| $C_{12-15}$ Alkylbenzoate | 2 | 2 | 2 | 2 | 2 | 2 | 2 | 2 |
| Dicaprylyl Ether | 2 | | 2 | | 2 | | 2 | |
| Dioctyl Butamido Triazone | | 2 | | 2 | | 2 | | 2 |
| Aniso Triazine | 2.00 | 3.00 | 2.00 | 3.00 | 2.00 | 3.00 | 2.00 | 3.00 |
| Polysilicone-15 | 5 | 5 | 5 | 5 | 5 | 5 | 5 | 5 |
| Octyltriazone | | 1 | | 1 | | 1 | | 1 |
| 4-Methylbenzylidene Camphor | | 1 | | 1 | | 1 | | 1 |
| Butyl Methoxydibenzoylmethane | 1 | 2 | 1 | 2 | 1 | 2 | 1 | 2 |
| Merocyanine of formula MC-08 | 3 | | | | | | | |
| Merocyanine of formula MC-08 | | 2 | | | | | | |
| Merocyanine of formula MC-09 | | | 3 | | | | | |
| Merocyanine of formula MC-09 | | | | 2 | | | | |
| Merocyanine of formula MC-10 | | | | | 3 | | | |
| Merocyanine of formula MC-10 | | | | | | 2 | | |
| Merocyanine of formula MC-11 | | | | | | | 3 | |
| Merocyanine of formula MC-11 | | | | | | | | 2 |
| Ethylhexylmethaxycinnamate | 5.0 | 8.0 | 5.0 | 8.0 | 5.0 | 8.0 | 5.0 | 8.0 |
| Aerosil R 972 | | | | | | | | |
| Preservative | 0.50 | 0.50 | 0.50 | 0.50 | 0.50 | 0.50 | 0.50 | 0.50 |
| Glycerin | 3.00 | 5.00 | 3.00 | 5.00 | 3.00 | 5.00 | 3.00 | 5.00 |

-continued

Examples 6.1-6.8

| | 6.1 Hydro dispersion | 6.2 Spray | 6.3 Hydro dispersion | 6.4 Spray | 6.5 Hydro dispersion | 6.6 Spray | 6.7 Hydro dispersion | 6.8 Spray |
|---|---|---|---|---|---|---|---|---|
| Xanthan Gum | 0.50 | | 0.50 | | 0.50 | | 0.50 | |
| Acrylates/C10-30 Alkyl Acrylate Crosspolymer (Pemulen TR1) | 0.30 | | 0.30 | | 0.30 | | 0.30 | |
| NaOH 45% | 0.30 | | 0.30 | | 0.30 | | 0.30 | |
| Water | ad 100.0 | ad 100.0 | ad 100.0 | ad 100.0 | ad 100.0 | ad 100.0 | ad 100.0 | ad 100.0 |

Examples 7.1: PIT - Sun Sprays

| | 7.1 | 7.1 | 7.1 | 7.1 |
|---|---|---|---|---|
| Glycerin Monostearate SE | 3.00 | 3.00 | 3.00 | 3.00 |
| Ceteareth-30 | 1.00 | 1.00 | 1.00 | 1.00 |
| Stearyl Alcohol | 3.00 | 3.00 | 3.00 | 3.00 |
| Aniso Triazine | 0.80 | 0.80 | 0.80 | 0.80 |
| Butyl Methoxydibenzoylmethane | 2.00 | 2.00 | 2.00 | 2.00 |
| Ethylhexyl Triazone | 3.00 | 3.00 | 3.00 | 3.00 |
| Octocrylene | 5.00 | 5.00 | 5.00 | 5.00 |
| Bisimidazylate | 0.50 | 0.50 | 0.50 | 0.50 |
| Butylene Glycol Dicaprylate/Dicaprate | 6.00 | 6.00 | 6.00 | 6.00 |
| Phenyl Trimethicone | 0.50 | 0.50 | 0.50 | 0.50 |
| Shea Butter | 3.50 | 3.50 | 3.50 | 3.50 |
| PVP Hexadecene Copolymer | 0.50 | 0.50 | 0.50 | 0.50 |
| Glycerin | 7.50 | 7.50 | 7.50 | 7.50 |
| Merocyanine of formula MC-08 | 3.50 | | | |
| Merocyanine of formula MC-09 | | 3.50 | | |
| Merocyanine of formula MC-10 | | | 3.50 | |
| Merocyanine of formula MC-11 | | | | 3.50 |
| Fucogel ® 1000 | 2.50 | 2.50 | 2.50 | 2.50 |
| Polyurethane | 0.50 | 0.50 | 0.50 | 0.50 |
| DMDM Hydantoin | 0.20 | 0.20 | 0.20 | 0.20 |
| Methylparaben | 0.15 | 0.15 | 0.15 | 0.15 |
| Phenoxyethanol | 1.00 | 1.00 | 1.00 | 1.00 |
| Aqua | ad 100 | ad 100 | ad 100 | ad 100 |

Example 7.2-7.4: O/W Sunscreen Emulsion

| | 7.2 | 7.3 | 7.4 | 7.2 | 7.3 | 7.4 | 7.2 | 7.3 | 7.4 | 7.2 | 7.3 | 7.4 |
|---|---|---|---|---|---|---|---|---|---|---|---|---|
| Glycerin Monostearate SE | 0.50 | 3.00 | 1.50 | 0.50 | 3.00 | 1.50 | 0.50 | 3.00 | 1.50 | 0.50 | 3.00 | 1.50 |
| Glyceryl Stearate Citrate | 2.00 | | | 2.00 | | | 2.00 | | | 2.00 | | |
| Stearic Acid | | | | | | | | | | | | |
| PEG-40 Stearate | 0.50 | | 2.00 | 0.50 | | 2.00 | 0.50 | | 2.00 | 0.50 | | 2.00 |
| Cetyl Phosphate | | | | | | | | | | | | |
| Stearyl Alkohol | | 3.00 | 2.00 | | 3.00 | 2.00 | | 3.00 | 2.00 | | 3.00 | 2.00 |
| Cetyl Alkohol | 2.50 | | | 2.50 | | | 2.50 | | | 2.50 | | |
| Butyl Methoxydibenzoylmethane | 1.00 | 2.00 | 2.00 | 1.00 | 2.00 | 2.00 | 1.00 | 2.00 | 2.00 | 1.00 | 2.00 | 2.00 |
| Dioctyl Butamido Triazone | | | 2.00 | | | 2.00 | | | 2.00 | | | 2.00 |
| Ethylhexyl Triazone | 4.00 | 3.00 | 2.00 | 4.00 | 3.00 | 2.00 | 4.00 | 3.00 | 2.00 | 4.00 | 3.00 | 2.00 |
| 4-Melhylbenzylidene Camphor | 4.00 | | 4.00 | 4.00 | | 4.00 | 4.00 | | 4.00 | 4.00 | | 4.00 |
| Dioctyl Butamido Triazone | 1.00 | | | 1.00 | | | 1.00 | | | 1.00 | | |
| Bisimidazylate | 1.00 | 0,50 | 1.00 | 1.00 | 0,50 | 1.00 | 1.00 | 0,50 | 1.00 | 1.00 | 0,50 | 1.00 |
| Phenylbenzmidazole Sulfonic Acid | 0:50 | | | 0:50 | | | 0:50 | | | 0:50 | | |
| Tilanium Dioxide | 1.00 | | 2.00 | 1.00 | | 2.00 | 1.00 | | 2.00 | 1.00 | | 2.00 |
| $C_{12-15}$ Alkylbenzoate | | | 7.00 | | | 7.00 | | | 7.00 | | | 7.00 |
| Dlcaprylyl Ether | | 3.50 | | | 3.50 | | | 3.50 | | | 3.50 | |
| Butylene Glycol Dicaprylate/Dicaprate | 5.00 | | | 5.00 | | | 5.00 | | | 5.00 | | |
| Dicaprylyl Carbonate | | 6.00 | 2.00 | | 6.00 | 2.00 | | 6.00 | 2.00 | | 6.00 | 2.00 |
| Dimethicone | | 1.00 | | | 1.00 | | | 1.00 | | | 1.00 | |
| Cetyl Dimethicone | 2.00 | | | 2.00 | | | 2.00 | | | 2.00 | | |
| PVP Hexadecene Copolymer | 0.50 | | | 0.50 | | | 0.50 | | | 0.50 | | |
| Xanthan Gum | 3;00 | | | 3;00 | | | 3;00 | | | 3;00 | | |
| Merocyanine of formula MC-08 | 0.80 | | | | | | | | | | | |
| Merocyanine of formula MC-08 | | 0.30 | | | | | | | | | | |
| Merocyanine of formula MC-08 | | | 2.80 | | | | | | | | | |
| Merocyanine of formula MC-09 | | | | 0.80 | | | | | | | | |
| Merocyanine of formula MC-09 | | | | | 0.30 | | | | | | | |
| Merocyanine of formula MC-09 | | | | | | 2.80 | | | | | | |
| Merocyanine of formula MC-10 | | | | | | | 0.80 | | | | | |
| Merocyanine of formula MC-10 | | | | | | | | 0.30 | | | | |
| Merocyanine of formula MC-10 | | | | | | | | | 2.80 | | | |
| Merocyanine of formula MC-11 | | | | | | | | | | 0.80 | | |
| Merocyanine of formula MC-11 | | | | | | | | | | | 0.30 | |
| Merocyanine of formula MC-11 | | | | | | | | | | | | 2.80 |
| Sodium Carbomer | | 0.10 | | | 0.10 | | | 0.10 | | 0.50 | | |
| Vitamin E Acetate | 0.50 | 0.25 | | 0.50 | 0.25 | | 0.50 | 0.25 | | 0.50 | 0.25 | |

Example 7.2-7.4: O/W Sunscreen Emulsion

| | 7.2 | 7.3 | 7.4 | 7.2 | 7.3 | 7.4 | 7.2 | 7.3 | 7.4 | 7.2 | 7.3 | 7.4 |
|---|---|---|---|---|---|---|---|---|---|---|---|---|
| Polyurethane | 0.50 | 1.50 | 1.00 | 0.50 | 1.50 | 1.00 | 0.50 | 1.50 | 1.00 | 0.50 | 1.50 | 1.00 |
| DMDM Hydantoin | | 0.40 | | | 0.40 | | | 0.40 | | | 0.40 | |
| Konkaben LM B 6 | | | 0.10 | | | 0.10 | | | 0.10 | 0.25 | | 0.10 |
| Methylparaben | 0.25 | 0.26 | | 0.25 | 0.26 | | 0.25 | 0.26 | | 1.00 | 0.26 | |
| Phenoxyethanol | 1.00 | | 0.40 | 1.00 | | 0.40 | 1.00 | | 0.40 | | | 0.40 |
| Ethanol | | 1.50 | | | 1.50 | | | 1.50 | | ad. 100 | 1.50 | |
| Water | ad. 100 | ad. 100 | ad 100 | ad. 100 | ad. 100 | ad 100 | ad. 100 | ad. 100 | ad 100 | ad. 100 | ad. 100 | ad 100 |

Example 7.5-7.6: Hydrodispersions

| | 7.5 | 7.6 | 7.5 | 7.6 | 7.5 | 7.6 | 7.5 | 7.6 |
|---|---|---|---|---|---|---|---|---|
| Ceteareth 20 | 1.00 | | 1.00 | | 1.00 | | 1.00 | |
| Celyl Alkohol | | 1.00 | | 1.00 | | 1.00 | | 1.00 |
| Acrylates/C10-30 Alkyl Acrylate Crosspolymer | 0.50 | 0..40 | 0.50 | 0..40 | 0.50 | 0..40 | 0.50 | 0..40 |
| Xanthan Gum | | 0.15 | | 0.15 | | 0.15 | | 0.15 |
| Butyl Methoxydibenzoylmethane | 1;00 | 2.00 | 1;00 | 2.00 | 1;00 | 2.00 | 1;00 | 2.00 |
| Ethylhexyl Triazone | 4.00 | 3.00 | 4.00 | 3.00 | 4.00 | 3.00 | 4.00 | 3.00 |
| 4-Methylbenzylidene Camphor | 4.00 | | 4.00 | | 4.00 | | 4.00 | |
| Octocrylene | | 4.00 | | 4.00 | | 4.00 | | 4.00 |
| Merocyanine of formula MC-08 | 1.00 | | | | | | | |
| Merocyanine of formula MC-08 | | 1.50 | | | | | | |
| Merocyanine of formula MC-09 | | | 1.00 | | | | | |
| Merocyanine of formula MC-09 | | | | 1.50 | | | | |
| Merocyanine of formula MC-10 | | | | | 1.00 | | | |
| Merocyanine of formula MC-10 | | | | | | 1.50 | | |
| Merocyanine of formula MC-11 | | | | | | | 1.00 | |
| Merocyanine of formula MC-11 | | | | | | | | 1.50 |
| Dioctyl Butamido Triazone | 1.00 | | 1.00 | | 1.00 | | 1.00 | |
| Bisimidazylate | 1.00 | 0.50 | 1.00 | 0.50 | 1.00 | 0.50 | 1.00 | 0.50 |
| Phenylbenzmidazole Sulfonic Acid | 0.50 | | 0.50 | | 0.50 | | 0.50 | |
| Titanium Dioxide | 0.50 | 2.00 | 0.50 | 2.00 | 0.50 | 2.00 | 0.50 | 2.00 |
| $C_{12-15}$ Alkylbenzoate | 2.00 | | 2.00 | | 2.00 | | 2.00 | |
| Butylene Glycol Dicaprylate/Dicaprate | 4.00 | 2:00 | 4.00 | 2:00 | 4.00 | 2:00 | 4.00 | 2:00 |
| Dicaprylyl Carbonate | | 6:00 | | 6:00 | | 6:00 | | 6:00 |
| Dimethicone | | 1;00 | | 1;00 | | 1;00 | | 1;00 |
| Phenyltrimethicone | 2.00 | | 2.00 | | 2.00 | | 2.00 | |
| PVP Hexadecene Copolymer | 0:50 | | 0:50 | | 0:50 | | 0:50 | |
| Octoxyglycerin | | 1:04 | | 1:04 | | 1:04 | | 1:04 |
| Glycerin | 3.00 | | 3.00 | | 3.00 | | 3.00 | |
| Glycine Soja | | 1.50 | | 1.50 | | 1.50 | | 1.50 |
| Vitamin E Acetate | 0;50 | 0.25 | 0;50 | 0.25 | 0;50 | 0.25 | 0;50 | 0.25 |
| Polyurethane | 0.15 | 1.50 | 0.15 | 1.50 | 0.15 | 1.50 | 0.15 | 1.50 |
| DEDM Hydantoin | | 0;40 | | 0;40 | | 0;40 | | 0;40 |
| Konkaben LM B db | | 0:20 | | 0:20 | | 0:20 | | 0:20 |
| Methylparben | 0;50 | 0.25 | 0;50 | 0.25 | 0;05 | 0.25 | 0;50 | 0.25 |
| Phenoxyethanal | 0.50 | | 0.50 | | 0.50 | | 0.50 | |
| Ethanol | 3.00 | 1.50 | 3.00 | 1.50 | 3.00 | 1.50 | 3.00 | 1.50 |
| Water | ad. 100 | ad. 100 | ad. 100 | ad. 100 | ad. 100 | ad. 100 | ad. 100 | ad. 100 |

Example 7.7-7.9: O/W Sunscreen Emulsions

| | 7.7 | 7.8 | 7.9 | 7.7 | 7.8 | 7.9 | 7.7 | 7.8 | 7.9 | 7.7 | 7.8 | 7.9 |
|---|---|---|---|---|---|---|---|---|---|---|---|---|
| Glycerin Monostearate SE | 0.50 | 3.00 | 1.50 | 0.50 | 3.00 | 1.50 | 0.50 | 3.00 | 1.50 | 0.50 | 3.00 | 1.50 |
| Glyceryl Stearate Citrate | 2.00 | | | 2.00 | | | 2.00 | | | 2.00 | | |
| PEG-40 Stearate | 0.50 | | 2.00 | 0.50 | | 2.00 | 0.50 | | 2.00 | 0.50 | | 2.00 |
| Stearyl Alcohol | | 3.00 | 2.00 | | 3.00 | 2.00 | | 3.00 | 2.00 | | 3.00 | 2.00 |
| Cetyl Alcohol | 2.50 | | | 2.50 | | | 2.50 | | | 2.50 | | |
| Butyl Methoxydibenzoylmethane | 1.00 | 2.00 | 2.00 | 1.00 | 2.00 | 2.00 | 1.00 | 2.00 | 2.00 | 1.00 | 2.00 | 2.00 |
| Dioctyl Butamido Triazone | | | 2.00 | | | 2.00 | | | 2.00 | | | 2.00 |
| Ethylhexyl Triazone | 4.00 | 3.00 | 2.00 | 4.00 | 3.00 | 2.00 | 4.00 | 3.00 | 2.00 | 4.00 | 3.00 | 2.00 |
| 4-Melhylbenrylidene Camphor | 4.00 | | 4.00 | 4.00 | | 4.00 | 4.00 | | 4.00 | 4.00 | | 4.00 |
| Dioctyl Butamido Triazone | 1.00 | | 1.00 | | | 1.00 | | | 1.00 | | | |
| Bisimidazylale | 1¡00 | 0.50 | 1.00 | 1¡00 | 0.50 | 1.00 | 1¡00 | 0.50 | 1.00 | 1¡00 | 0.50 | 1.00 |

-continued

Example 7.7-7.9: O/W Sunscreen Emulsions

| | 7.7 | 7.8 | 7.9 | 7.7 | 7.8 | 7.9 | 7.7 | 7.8 | 7.9 | 7.7 | 7.8 | 7.9 |
|---|---|---|---|---|---|---|---|---|---|---|---|---|
| Phenylbenzmidazole Sulfonic Acid | 0:50 | | | 0:50 | | | 0:50 | | | 0:50 | | |
| Titanium Dioxide | 1.00 | | 2.00 | 1.00 | | 2.00 | 1.00 | | 2.00 | 1.00 | | 2.00 |
| $C_{12-15}$ Alkylbenzoate | | | 7.00 | | | 7.00 | | | 7.00 | | | 7.00 |
| Dicaprylyl Ether | | 3.50 | | | 3.50 | | | 3.50 | | | 3.50 | |
| Butylene Glycol Dicaprylate/Dicaprate | 5.00 | | | 5.00 | | | 5.00 | | | 5.00 | | |
| Dicaprylyl Carbonate | | 6.00 | 2.00 | | 6.00 | 2.00 | | 6.00 | 2.00 | | 6.00 | 2.00 |
| Dimethicone | | 1.00 | | | 1.00 | | | 1.00 | | | 1.00 | |
| Cetyl Dimethicone | 2.00 | | | 2.00 | | | 2.00 | | | 2.00 | | |
| PVP Hexadecene Copolymer | 0.50 | | | 0.50 | | | 0.50 | | | 0.50 | | |
| Glycerin | 3.00 | | | 3.00 | | | 3.00 | | | 3.00 | | |
| Merocyanine of formula MC-08 | 2.00 | | | | | | | | | | | |
| Merocyanine of formula MC-08 | | 5.00 | | | | | | | | | | |
| Merocyanine of formula MC-08 | | | 0.80 | | | | | | | | | |
| Merocyanine of formula MC-09 | | | | 2.00 | | | | | | | | |
| Merocyanine of formula MC-09 | | | | | 5.00 | | | | | | | |
| Merocyanine of formula MC-09 | | | | | | 0.80 | | | | | | |
| Merocyanine of formula MC-10 | | | | | | | 2.00 | | | | | |
| Merocyanine of formula MC-10 | | | | | | | | 5.00 | | | | |
| Merocyanine of formula MC-10 | | | | | | | | | 0.80 | | | |
| Merocyanine of formula MC-11 | | | | | | | | | | 2.00 | | |
| Merocyanine of formula MC-11 | | | | | | | | | | | 5.00 | |
| Merocyanine of formula MC-11 | | | | | | | | | | | | 0.80 |
| Xanthan Gum | 0.15 | 0.05 | | 0.15 | 0.05 | | 0.15 | 0.05 | | 0.15 | 0.05 | |
| Sodium Carbomer | | 0.10 | | | 0.10 | | | 0.10 | | | 0.10 | |
| Vitamin E Acetate | 0.50 | 0.25 | | 0.50 | 0.25 | | 0.50 | 0.25 | | 0.50 | 0.25 | |
| Polyurethane | 0.50 | 1.50 | 1.00 | 0.50 | 1.50 | 1.00 | 0.50 | 1.50 | 1.00 | 0.50 | 1.50 | 1.00 |
| DEDM Hydantoin | | 0.40 | | | 0.40 | | | 0.40 | | | 0.40 | |
| Konkaben LMB | | | 0.10 | | | 0.10 | | | 0.10 | | | 0.10 |
| Methylparaben | 0.15 | 0.25 | | 0.15 | 0.25 | | 0.15 | 0.25 | | 0.15 | 0.25 | |
| Phenoxyethanol | 1.00 | | 0.40 | 1.00 | | 0.40 | 1.00 | | 0.40 | 1.00 | | 0.40 |
| Ethanol | | 1.50 | | | 1.50 | | | 1.50 | | | 1.50 | |
| Water | ad 100 | ad 100 | ad 100 | ad 100 | ad 100 | ad 100 | ad 100 | ad 100 | ad 100 | ad 100 | ad 100 | ad 100 |

Examples 7.10-7.11: W/O Sunscreen

| | 7.10 | 7.11 | 7.10 | 7.11 | 7.10 | 7.11 | 7.10 | 7.11 |
|---|---|---|---|---|---|---|---|---|
| Cetyldimethicone Copolyol | | 4.00 | | 4.00 | | 4.00 | | 4.00 |
| PEG-30 Dipolyhydroxystearate | 5.00 | | 5.00 | | 5.00 | | 5.00 | |
| Ethylhexyl Methoxycinnamate | | 5.00 | | 5.00 | | 5.00 | | 5.00 |
| Aniso Triazine | | 2.00 | | 2.00 | | 2.00 | | 2.00 |
| Butyl Methoxydibenzoylmethane | 2.00 | 1.00 | 2.00 | 1.00 | 2.00 | 1.00 | 2.00 | 1.00 |
| Ethylhexyl Triazone | 3.00 | 4.00 | 3.00 | 4.00 | 3.00 | 4.00 | 3.00 | 4.00 |
| 4-Methylbenzylidene Camphor | | 4.00 | | 4.00 | | 4.00 | | 4.00 |
| Octocrylene | 4.00 | | 4.00 | | 4.00 | | 4.00 | |
| Dioctyl Butamido Triazone | | 2.00 | | 2.00 | | 2.00 | | 2.00 |
| Bisimidazylate | 0.50 | | 0.50 | | 0.50 | | 0.50 | |
| Phenylbenzmidazole Sulfonic Acid | | 3.00 | | 3.00 | | 3.00 | | 3.00 |
| Titanium Dioxide | 1.50 | | 1.50 | | 1.50 | | 1.50 | |
| Mineral Oil | 10.0 | | 10.0 | | 10.0 | | 10.0 | |
| $C_{12-15}$ Alkylbenzoate | | 9.00 | | 9.00 | | 9.00 | | 9.00 |
| Butylene Glycol Dicaprylate/Dicaprate | 2.00 | 8.00 | 2.00 | 8.00 | 2.00 | 8.00 | 2.00 | 8.00 |
| Dicaprylyl Carbonate | 6.00 | | 6.00 | | 6.00 | | 6.00 | |
| Dimethicone | 1.00 | 5.00 | 1.00 | 5.00 | 1.00 | 5.00 | 1.00 | 5.00 |
| Shea Butter | 3.00 | | 3.00 | | 3.00 | | 3.00 | |
| PVP Hexadecene Copolymer | | 0.50 | | 0.50 | | 0.50 | | 0.50 |
| Octoxyclycerin | 1.00 | | 1.00 | | 1.00 | | 1.00 | |
| Glycerin | | 7.50 | | 7.50 | | 7.50 | | 7.50 |
| Glycerin Soya | 1.50 | | 1.50 | | 1.50 | | 1.50 | |
| $MgSO_4$ | | 0.5 | | 0.5 | | 0.5 | | 0.5 |
| $MgCl_2$ | 1.00 | | 1.00 | | 1.00 | | 1.00 | |
| Vitamine E Acetate | 0.25 | | 0.25 | | 0.25 | | 0.25 | |
| Merocyanine of formula MC-08 | 0.50 | | | | | | 0.50 | |
| Merocyanine of formula MC-08 | | 0.30 | | | | | | |
| Merocyanine of formula MC-09 | | | 0.50 | | | | | |
| Merocyanine of formula MC-09 | | | | 0.30 | | | | |
| Merocyanine of formula MC-10 | | | | | 0.50 | | | |
| Merocyanine of formula MC-10 | | | | | | 0.30 | | |
| Merocyanine of formula MC-11 | | | | | | | | 0.50 |

Examples 7.10-7.11: W/O Sunscreen

|  | 7.10 | 7.11 | 7.10 | 7.11 | 7.10 | 7.11 | 7.10 | 7.11 |
|---|---|---|---|---|---|---|---|---|
| Merocyanine of formula MC-11 |  |  |  |  |  |  |  | 0.30 |
| Polyurethane | 1.50 | 1.00 | 1.50 | 1.00 | 1.50 | 1.00 | 1.50 | 1.00 |
| DMDM Hydantoin | 0.40 | 0.20 | 0.40 | 0.20 | 0.40 | 0.20 | 0.40 | 0.20 |
| Methylparaben | 0.25 | 0.15 | 0.25 | 0.15 | 0.25 | 0.15 | 0.25 | 0.15 |
| Phenoxyethanol |  | 1.00 |  | 1.00 |  | 1.00 |  | 1.00 |
| Ethanol | 1.50 |  | 1.50 |  | 1.50 |  | 1.50 |  |
| Water | ad 100 | ad 100 | ad 100 | ad 100 | ad 100 | ad 100 | ad 100 | ad 100 |

Examples 8.1

|  | 8.1 | 8.1 | 8.1 | 8.1 |
|---|---|---|---|---|
| Sucrose Distearate | 2 | 2 | 2 | 2 |
| Cetearyl Alcohol | 4.5 | 4.5 | 4.5 | 4.5 |
| Butylene Glycol Dicaprylate/Dicaprate | 5 | 5 | 5 | 5 |
| Caprylic Acid/Capric Acid Triglyceride | 1.5 | 1.5 | 1.5 | 1.5 |
| Dimethicone | 1 | 1 | 1 | 1 |
| Phenyl Trimethicone | 1 | 1 | 1 | 1 |
| Butyl Methoxydibenzoylmethane | 2 | 2 | 2 | 2 |
| Merocyanine of formula MC-08 | 2.00 |  |  |  |
| Merocyanine of formula MC-09 |  | 2.00 |  |  |
| Merocyanine of formula MC-10 |  |  | 2.00 |  |
| Merocyanine of formula MC-11 |  |  |  | 2.00 |
| Bisimidazylate | 0.5 | 0.5 | 0.5 | 0.5 |
| Dioctyl Butamido Triazone | 2 | 2 | 2 | 2 |
| 4-Methylbenzylidene Camphor | 2 | 2 | 2 | 2 |
| Titanium Dioxide | 1 | 1 | 1 | 1 |
| Trisodium EDTA | 1 | 1 | 1 | 1 |
| Tricontayl PVP | 1 | 1 | 1 | 1 |
| Tocopheryl Acetate | 0.5 | 0.5 | 0.5 | 0.5 |
| α-Glucosylrutin + Isoquercitrin | 0.3 | 0.3 | 0.3 | 0.3 |
| Phenoxyethanol | 0.5 | 0.5 | 0.5 | 0.5 |
| Carbomer | 0.3 | 0.3 | 0.3 | 0.3 |
| Iodopropynyl Butylcarbamate | 0.1 | 0.1 | 0.1 | 0.1 |
| NaOH 45% | 0.25 | 0.25 | 0.25 | 0.25 |
| Glycerin | 2 | 2 | 2 | 2 |
| Butylene Glycol | 3 | 3 | 3 | 3 |
| DMDM Hydantoin | 0.05 | 0.05 | 0.05 | 0.05 |
| Alcohol denat. | 3 | 3 | 3 | 3 |
| Distarch Phosphate | 5 | 5 | 5 | 5 |
| Parfum | q.s. | q.s. | q.s. | q.s. |
| Water | ad 100 | ad 100 | ad 100 | ad 100 |

Example 9.1: O/W Lotion

|  | % b.w. | % b.w. | % b.w. | % b.w. |
|---|---|---|---|---|
| Glycerin Sstearate | 3.50 | 3.50 | 3.50 | 3.50 |
| Stearic Acid | 1.80 | 1.80 | 1.80 | 1.80 |
| Cetylstearyl Alcohol | 0.50 | 0.50 | 0.50 | 0.50 |
| NaOH 45% | 0.20 | 0.20 | 0.20 | 0.20 |
| Octyldodecanol | 7.0 | 7.0 | 7.0 | 7.0 |
| Dicaprylyl Ether | 8.0 | 8.0 | 8.0 | 8.0 |
| SMT | 3.00 | 3.00 | 3.00 | 3.00 |
| Titanium Dioxide | 2.00 | 2.00 | 2.00 | 2.00 |
| Merocyanine of formula MC-08 | 2.60 |  |  |  |
| Merocyanine of formula MC-09 |  | 2.60 |  |  |
| Merocyanine of formula MC-10 |  |  | 2.60 |  |
| Merocyanine of formula MC-11 |  |  |  | 2.60 |
| Butyl Methoxydibenzoylmethane | 2.00 | 2.00 | 2.00 | 2.00 |
| 4-Methylbenzylidene Camphor | 1.00 | 1.00 | 1.00 | 1.00 |
| Dioctylmaleate | 6.00 | 6.00 | 6.00 | 6.00 |
| Carbomer | 0.20 | 0.20 | 0.20 | 0.20 |
| Preservatives | q.s. | q.s. | q.s. | q.s. |
| Parfum | q.s. | q.s. | q.s. | q.s. |
| Water | ad 100 | ad 100 | ad 100 | ad 100 |

Example 10.1: O/W Creme

|  | % b.w. | % b.w. | % b.w. | % b.w. |
|---|---|---|---|---|
| Glyceryl Stearate | 3.50 | 3.50 | 3.50 | 3.50 |
| Stearic Acid | 3.5 | 3.5 | 3.5 | 3.5 |
| Butylene Glycol | 5.0 | 5.0 | 5.0 | 5.0 |
| Cetylstearylalcohol | 3.00 | 3.00 | 3.00 | 3.00 |
| Merocyanine of formula MC-08 | 2.00 |  |  |  |
| Merocyanine of formula MC-09 |  | 2.00 |  |  |
| Merocyanine of formula MC-10 |  |  | 2.00 |  |
| Merocyanine of formula MC-11 |  |  |  | 2.00 |
| NaOH 45% | 0.15 | 0.15 | 0.15 | 0.15 |
| $C_{12-15}$ Alkylbenzoate | 10.0 | 10.0 | 10.0 | 10.0 |
| Ethylhexyl Triazone | 4.0 | 4.0 | 4.0 | 4.0 |
| Octocrylene | 10.0 | 10.0 | 10.0 | 10.0 |
| Titanium Dioxide | 2.00 | 2.00 | 2.00 | 2.00 |
| Butyl Methoxydibenzoylmethane | 2.0 | 2.0 | 2.0 | 2.0 |
| 4-Methylbenzylidene Camphor | 1.0 | 1.0 | 1.0 | 1.0 |
| Dioctylmaleate | 6.00 | 6.00 | 6.00 | 6.00 |
| Carbomer | 0.20 | 0.20 | 0.20 | 0.20 |
| Preservatives | q.s. | q.s. | q.s. | q.s. |
| Parfum | q.s. | q.s. | q.s. | q.s. |
| Water | ad 100 | ad 100 | ad 100 | ad 100 |

Example 11.1: W/O Lotion

|  | % b.w. | % b.w. | % b.w. | % b.w. |
|---|---|---|---|---|
| Polyglyceryl-2-Polyhydroxystearate | 3.50 | 3.50 | 3.50 | 3.50 |
| Polyglyceryl-3-Diisostearate | 3.50 | 3.50 | 3.50 | 3.50 |
| Butylene Glycol | 5.00 | 5.00 | 5.00 | 5.00 |
| Ceresin | 3.00 | 3.00 | 3.00 | 3.00 |
| NaOH 45% | 0.35 | 0.35 | 0.35 | 0.35 |
| $C_{12-15}$ Alkylbenzoate | 10.0 | 10.0 | 10.0 | 10.0 |
| Ethylhexyl Triazone | 4.00 | 4.00 | 4.00 | 4.00 |
| Titanium Dioxide | 2.00 | 2.00 | 2.00 | 2.00 |
| Butyl Methoxydibenzoylmethane | 2.00 | 2.00 | 2.00 | 2.00 |
| 4-Methylbenzylidene Camphor | 1.00 | 1.00 | 1.00 | 1.00 |
| Merocyanine of formula MC-08 | 1.50 |  |  |  |
| Merocyanine of formula MC-09 |  | 1.50 |  |  |
| Merocyanine of formula MC-10 |  |  | 1.50 |  |
| Merocyanine of formula MC-11 |  |  |  | 1.50 |
| Dioctylmaleate | 6.00 | 6.00 | 6.00 | 6.00 |
| Vaseline | 2.00 | 2.00 | 2.00 | 2.00 |
| Preservatives | q.s. | q.s. | q.s. | q.s. |

Example 11.1: W/O Lotion

|  | % b.w. | % b.w. | % b.w. | % b.w. |
|---|---|---|---|---|
| Parfum | q.s. | q.s. | q.s. | q.s. |
| Water | ad 100 | ad 100 | ad 100 | ad 100 |

Example 12.1:

|  | % b.w. | % b.w. | % b.w. | % b.w. |
|---|---|---|---|---|
| Stearic Acid | 1.50 | 1.50 | 1.50 | 1.50 |
| Glycerin Monostearate | 0.50 | 0.50 | 0.50 | 0.50 |
| Bis-Ethylhexyloxyphenol Methoxyphenyl Triazine (Tinosorb S) | 4.00 | 4.00 | 4.00 | 4.00 |
| Butylene Glycol Dicaprylate/Dicaprate | 5.0 | 5.0 | 5.0 | 5.0 |
| Stearyl Heptanoate/Caprylate | 2.00 | 2.00 | 2.00 | 2.00 |
| Silicon Oil | 5.00 | 5.00 | 5.00 | 5.00 |
| Isohexadecane | 2.00 | 2.00 | 2.00 | 2.00 |
| 4,4',4''-(1,3,5-Triazine-2,4,6-triyltriimino)-tris-benzoic acid tris(2-ethylhexylester) | 1.0 | 1.0 | 1.0 | 1.0 |
| 4-Methylbenzylidene Camphor | 4.00 | 4.00 | 4.00 | 4.00 |
| Butyl Methoxydibenzoylmethane | 2.00 | 2.00 | 2.00 | 2.00 |
| Cetyl Stearyl Alcohol | 0.50 | 0.50 | 0.50 | 0.50 |
| Vitamine E Acetate | 0.50 | 0.50 | 0.50 | 0.50 |
| Preservatives, Dyes | q.s. | q.s. | q.s. | q.s. |
| NaOH 45% | 0.20 | 0.20 | 0.20 | 0.20 |
| Carbomer | 3.00 | 3.00 | 3.00 | 3.00 |
| Glycerin | 3.00 | 3.00 | 3.00 | 3.00 |
| Merocyanine of formula MC-08 | 5.80 |  |  |  |
| Merocyanine of formula MC-09 |  | 5.80 |  |  |
| Merocyanine of formula MC-10 |  |  | 5.80 |  |
| Merocyanine of formula MC-10 |  |  |  | 5.80 |
| EDTA Solution | 1.00 | 1.00 | 1.00 | 1.00 |
| Water | ad 100 | ad 100 | ad 100 | ad 100 |

Example 13.1: O/W Emulsion

|  | % b.w. | % b.w. | % b.w. | % b.w. |
|---|---|---|---|---|
| Stearic Acid | 1.50 | 1.50 | 1.50 | 1.50 |
| Glycerin Monostearate | 3.00 | 3.00 | 3.00 | 3.00 |
| Caprylic Acid/Capric Acid Triglyceride | 5.0 | 5.0 | 5.0 | 5.0 |
| Dicaprylyl Ether | 5.0 | 5.0 | 5.0 | 5.0 |
| Dimethicone | 1.00 | 1.00 | 1.00 | 1.00 |
| Butylene Glycol Dicprylate/dicaprate | 2.00 | 2.00 | 2.00 | 2.00 |
| $C_{12-15}$ Alkylbenzoate | 3.00 | 3.00 | 3.00 | 3.00 |
| Vitamine E Acetate | 0.50 | 0.50 | 0.50 | 0.50 |
| Dioctyl Butamido Triazone | 2.0 | 2.0 | 2.0 | 2.0 |
| Aniso Triazine | 2.00 | 2.00 | 2.00 | 2.00 |
| Repellent 3535 | 5.00 | 5.00 | 5.00 | 5.00 |
| Octyl Triazone | 1.00 | 1.00 | 1.00 | 1.00 |
| 4-Methylbenzylidene Camphor | 4.00 | 4.00 | 4.00 | 4.00 |
| Butyl Methoxy dibenzoylmethane | 2.00 | 2.00 | 2.00 | 2.00 |
| Titanium Dioxide | 1.00 | 1.00 | 1.00 | 1.00 |
| Glycerin | 5.00 | 5.00 | 5.00 | 5.00 |
| Merocyanine of formula MC-08 | 3.50 |  |  |  |
| Merocyanine of formula MC-09 |  | 3.50 |  |  |
| Merocyanine of formula MC-10 |  |  | 3.50 |  |
| Merocyanine of formula MC-10 |  |  |  | 3.50 |
| Crosslinked Acrylic Acid/($C_{10-30}$) Alkyl Acrylate Copolymer | 0.20 | 0.20 | 0.20 | 0.20 |
| NaOH 45% | 0.7 | 0.7 | 0.7 | 0.7 |
| Preservatives, Parfum, Dyes | q.s. | q.s. | q.s. | q.s. |
| Water | ad 100 | ad 100 | ad 100 | ad 100 |

Example 14.1: O/W Emulsion

|  | % b.w. | % b.w. | % b.w. | % b.w. |
|---|---|---|---|---|
| Sorbitan Stearate | 3.00 | 3.00 | 3.00 | 3.00 |
| Polyglyceryl-2 Dipolyhydroxy-stearate | 1.50 | 1.50 | 1.50 | 1.50 |
| Octyldodecanol | 10.00 | 10.00 | 10.00 | 10.00 |
| Dicaprylyl Ether | 5.00 | 5.00 | 5.00 | 5.00 |
| Cetylstearylisononanoate | 2.00 | 2.00 | 2.00 | 2.00 |
| Butylene Glycol Dicaprylate/Dicaprate | 5.00 | 5.00 | 5.00 | 5.00 |
| Vitamine E Acetate | 0.50 | 0.50 | 0.50 | 0.50 |
| Dioctyl Butamido Triazone | 6.00 | 6.00 | 6.00 | 6.00 |
| Repellent 3535 | 10.00 | 10.00 | 10.00 | 10.00 |
| Octyltriazone | 4.00 | 4.00 | 4.00 | 4.00 |
| Butyl Methoxydibenzoylmethane | 3.00 | 3.00 | 3.00 | 3.00 |
| Glycerin | 10.00 | 10.00 | 10.00 | 10.00 |
| Merocyanine of formula MC-08 | 1.80 |  |  |  |
| Merocyanine of formula MC-09 |  | 1.80 |  |  |
| Merocyanine of formula MC-10 |  |  | 1.80 |  |
| Merocyanine of formua MC-11 |  |  |  | 1.80 |
| Xanthan Gum | 0.20 | 0.20 | 0.20 | 0.20 |
| Phenylbenzimidazole Sulfonic Acid | 2.00 | 2.00 | 2.00 | 2.00 |
| NaOH 45% | 1.20 | 1.20 | 1.20 | 1.20 |
| Preservatives, Parfum, Dyes | q.s. | q.s. | q.s. | q.s. |
| Water | ad 100 | ad 100 | ad 100 | ad 100 |

Example 15.1: W/O Emulsion

|  | % b.w. | % b.w. | % b.w. | % b.w. |
|---|---|---|---|---|
| Cetyldimethicone Copolyol | 5.00 | 5.00 | 5.00 | 5.00 |
| Dimethicone | 5.00 | 5.00 | 5.00 | 5.00 |
| Isohexadecane | 2.00 | 2.00 | 2.00 | 2.00 |
| Butylene Glycol Dicaprylate/Dicaprate | 8.00 | 8.00 | 8.00 | 8.00 |
| $C_{12-15}$ Alkylbenzoate | 5.00 | 5.00 | 5.00 | 5.00 |
| Dioctyl Butamido Triazone | 2.00 | 2.00 | 2.00 | 2.00 |
| Aniso Triazine | 2.00 | 2.00 | 2.00 | 2.00 |
| Repellent 3535 | 10.00 | 10.00 | 10.00 | 10.00 |
| Octyltriazone | 1.00 | 1.00 | 1.00 | 1.00 |
| 4-Methylbenzylidene Camphor | 4.00 | 4.00 | 4.00 | 4.00 |
| Butyl Methoxydibenzoylmethane | 2.00 | 2.00 | 2.00 | 2.00 |
| Titanium Dioxide | 2.00 | 2.00 | 2.00 | 2.00 |
| Merocyanine of formula MC-08 | 2.50 |  |  |  |
| Merocyanine of formula MC-09 |  | 2.50 |  |  |
| Merocyanine of formula MC-10 |  |  | 2.50 |  |
| Merocyanine of formula MC-11 |  |  |  | 2.50 |
| Glycerin | 5.00 | 5.00 | 5.00 | 5.00 |
| NaCl | 1.00 | 1.00 | 1.00 | 1.00 |
| Phenylbenzimidazole Sulfonic Acid | 4.00 | 4.00 | 4.00 | 4.00 |
| NaOH 45% | 1.30 | 1.30 | 1.30 | 1.30 |
| Preservatives, Parfum, Dyes | q.s. | q.s. | q.s. | q.s. |
| Water | ad 100 | ad 100 | ad 100 | ad 100 |

Example 16.1: Spray

|  | % b.w. | % b.w. | % b.w. | % b.w. |
|---|---|---|---|---|
| Glycerin Monostearate | 4.00 | 4.00 | 4.00 | 4.00 |
| Ceth 12 | 1.50 | 1.50 | 1.50 | 1.50 |
| Caprylic Acid/Capric Acid Triglyceride | 2.00 | 2.00 | 2.00 | 2.00 |
| Mineral Oil | 5.00 | 5.00 | 5.00 | 5.00 |
| Dioctyl Butamido Triazone | 0.50 | 0.50 | 0.50 | 0.50 |
| Repellent 3535 | 2.00 | 2.00 | 2.00 | 2.00 |
| Octyltriazone | 1.00 | 1.00 | 1.00 | 1.00 |
| Butyl Methoxydibenzoylmethane | 1.00 | 1.00 | 1.00 | 1.00 |
| Glycerin | 10.00 | 10.00 | 10.00 | 10.00 |
| Merocyanine of formula MC-08 | 1.50 |  |  |  |

| Example 16.1: Spray | % b.w. | % b.w. | % b.w. | % b.w. |
|---|---|---|---|---|
| Merocyanine of formula MC-09 | | 1.50 | | |
| Merocyanine of formula MC-10 | | | 1.50 | |
| Merocyanine of formula MC-11 | | | | 1.50 |
| Phenylbenzimidazole Sulfonic Acid | 1.00 | 1.00 | 1.00 | 1.00 |
| NaOH 45% | 0.40 | 0.40 | 0.40 | 0.40 |
| Preservatives, Parfum, Dyes | q.s. | q.s. | q.s. | q.s. |
| Water | ad 100 | ad 100 | ad 100 | ad 100 |

| Examples 17.1 | 17.1 | 17.1 | 17.1 | 17.1 |
|---|---|---|---|---|
| Caprylic Acid/Capric Acid Triglyceride | 8 | 8 | 8 | 8 |
| Butylene Glycol Dicaprylate/Dicaprate | 8 | 8 | 8 | 8 |
| C18-36 Triglyceride | 1.5 | 1.5 | 1.5 | 1.5 |
| Phenyl Trimethicone | 1 | 1 | 1 | 1 |
| PVP Hexadecene Copolymer | 2.5 | 2.5 | 2.5 | 2.5 |
| Octyl Triazone | 2 | 2 | 2 | 2 |
| 4-Methylbenzylidene Camphor | 4 | 4 | 4 | 4 |
| Merocyanine of formula MC-08 | 3 | | | |
| Merocyanine of formula MC-09 | | 3 | | |
| Merocyanine of formula MC-10 | | | 3 | |
| Merocyanine of formula MC-11 | | | | 3 |
| Ethylhexyl Methoxycinnamate | 4 | 4 | 4 | 4 |
| Butyl Methoxydibenzoylmethane | 2 | 2 | 2 | 2 |
| Vitamine E Acetate | 0.3 | 0.3 | 0.3 | 0.3 |
| Phenylbenzimidazole Sulfonic Acid | 1 | 1 | 1 | 1 |
| NaOH 45% | 0.3 | 0.3 | 0.3 | 0.3 |
| Glycerin | 3 | 3 | 3 | 3 |
| Preservatives | 0.5 | 0.5 | 0.5 | 0.5 |
| Water | ad 100 | ad 100 | ad 100 | ad 100 |

| Example 17.2 | % b.w. | % b.w. | % b.w. | % b.w. |
|---|---|---|---|---|
| Ricinus Oil | 2.00 | 2.00 | 2.00 | 2.00 |
| Butylene Glycol Dicaprylate/Dicaprate | 10.00 | 10.00 | 10.00 | 10.00 |
| $C_{12-15}$ Alkylbenzoate | 5.00 | 5.00 | 5.00 | 5.00 |
| Octyltriazone | 4.00 | 4.00 | 4.00 | 4.00 |
| 4-Methylbenzylidene Camphor | 4.00 | 4.00 | 4.00 | 4.00 |
| Butyl Methoxydibenzoylmethane | 2.00 | 2.00 | 2.00 | 2.00 |
| Merocyanine of formula MC-08 | 1.50 | | | |
| Merocyanine of formula MC-09 | | 1.50 | | |
| Merocyanine of formula MC-10 | | | 1.50 | |
| Merocyanine of formula MC-11 | | | | 1.50 |
| C18-36 Triglyceride | 2.00 | 2.00 | 2.00 | 2.00 |
| C16-24 Triglyceride | 2.00 | 2.00 | 2.00 | 2.00 |
| Glycerin | 10.00 | 10.00 | 10.00 | 10.00 |
| Xanthan Gum | 0.20 | 0.20 | 0.20 | 0.20 |
| Crosslinked Acrylic Acid/($C_{10-30}$) Alkyl Acrylate Copolymer | 0.50 | 0.50 | 0.50 | 0.50 |
| Phenylbenzimidazole Sulfonic Acid | 2.00 | 2.00 | 2.00 | 2.00 |
| NaOH 45% | 1.20 | 1.20 | 1.20 | 1.20 |
| Preservatives, Parfum, Dyes | q.s. | q.s. | q.s. | q.s. |
| Water | ad 100 | ad 100 | ad 100 | ad 100 |

| Example 17.3 | % b.w. | % b.w. | % b.w. | % b.w. |
|---|---|---|---|---|
| Caprylic Acid/Capric Acid Triglyceride | 5.00 | 5.00 | 5.00 | 5.00 |
| Octyldodecanol | 5.00 | 5.00 | 5.00 | 5.00 |
| Butylene Glycol Dicaprylate/Dicaprate | 5.00 | 5.00 | 5.00 | 5.00 |
| Octyltriazone | 4.00 | 4.00 | 4.00 | 4.00 |
| Dioctyl Butamido Triazone | 4.00 | 4.00 | 4.00 | 4.00 |
| 4-Methylbenzylidene Camphor | 4.00 | 4.00 | 4.00 | 4.00 |
| Butyl Methoxydibenzoylmethane | 4.00 | 4.00 | 4.00 | 4.00 |
| Titanium Dioxide | 2.00 | 2.00 | 2.00 | 2.00 |
| C18-36 Triglyceride | 3.00 | 3.00 | 3.00 | 3.00 |
| C16 Triglyceride | 1.00 | 1.00 | 1.00 | 1.00 |
| Glycerin | 5.00 | 5.00 | 5.00 | 5.00 |
| Merocyanine of formula MC-08 | 1.50 | | | |
| Merocyanine of formula MC-09 | | 1.50 | | |
| Merocyanine of formula MC-10 | | | 1.50 | |
| Merocyanine of formula MC-11 | | | | 1.50 |
| Xanthan Gum | 0.20 | 0.20 | 0.20 | 0.20 |
| Hydroxypropylmethylcellulose | 0.20 | 0.20 | 0.20 | 0.20 |
| Phenylbenzimidazole Sulfonic Acid | 4.00 | 4.00 | 4.00 | 4.00 |
| NaOH 45% | 1.30 | 1.30 | 1.30 | 1.30 |
| Water | ad 100 | ad 100 | ad 100 | ad 100 |

| Examples 18.1 | % b.w. | % b.w. | % b.w. | % b.w. |
|---|---|---|---|---|
| Cetyl Dimethicone Copolyol | 6.00 | 6.00 | 6.00 | 6.00 |
| Mineral Oil | 4.00 | 4.00 | 4.00 | 4.00 |
| Caprylic Acid/Capric Acid Triglyceride | 6.00 | 6.00 | 6.00 | 6.00 |
| $C_{12-15}$ Alkylbenzoate | 5.00 | 5.00 | 5.00 | 5.00 |
| Butylene Glycol Dicaprylate/Dicaprate | 10.00 | 10.00 | 10.00 | 10.00 |
| $MgSO_4$ | 0.70 | 0.70 | 0.70 | 0.70 |
| Decylglucoside | 0.20 | 0.20 | 0.20 | 0.20 |
| Butyl Methoxydibenzoylmethane | 2.00 | 2.00 | 2.00 | 2.00 |
| 4-Methylbenzylidene Camphor | 4.00 | 4.00 | 4.00 | 4.00 |
| BEMBT | 2.00 | 2.00 | 2.00 | 2.00 |
| Titanium Dioxide | 3.00 | | | |
| Merocyanine of formula MC-08 | | | | |
| Merocyanine of formula MC-09 | | 3.00 | | |
| Merocyanine of formula MC-10 | | | 3.00 | |
| Merocyanine of formula MC-11 | | | | 3.00 |
| Phenylbenzimidazole Sulfonic Acid | 1.00 | 1.00 | 1.00 | 1.00 |
| NaOH 45% | 0.30 | 0.30 | 0.30 | 0.30 |
| EDTA Solution | 1.00 | 1.00 | 1.00 | 1.00 |
| Preservatives, Parfum, Dyes | q.s. | q.s. | q.s. | q.s. |
| Water | ad 100 | ad 100 | ad 100 | ad 100 |

| Examples 18.2 | % b.w. | % b.w. | % b.w. | % b.w. |
|---|---|---|---|---|
| Cetyl Dimethicone Copolyol | 6.00 | 6.00 | 6.00 | 6.00 |
| Mineral Oil | 4.00 | 4.00 | 4.00 | 4.00 |
| Caprylic Acid/Capric Acid Triglyceride | 6.00 | 6.00 | 6.00 | 6.00 |
| $C_{12-15}$ Alkylbenzoate | 5.00 | 5.00 | 5.00 | 5.00 |
| Butylene Glycol Dicaprylate/Dicaprate | 10.00 | 10.00 | 10.00 | 10.00 |
| Glycerin | 5.00 | 5.00 | 5.00 | 5.00 |
| $MgSO_4$ | 0.70 | 0.70 | 0.70 | 0.70 |
| Cetylstearylglucoside | 0.20 | 0.20 | 0.20 | 0.20 |
| Butyl Methoxydibenzoylmethane | 2.00 | 2.00 | 2.00 | 2.00 |
| 4-Methylbenzylidene Camphor | 4.00 | 4.00 | 4.00 | 4.00 |
| BEMBT | 2.00 | 2.00 | 2.00 | 2.00 |
| Merocyanine of formula MC-08 | 0.50 | | | |
| Merocyanine of formula MC-09 | | 0.50 | | |

| Examples 18.2 | % b.w. | % b.w. | % b.w. | % b.w. |
|---|---|---|---|---|
| Merocyanine of formula MC-10 | | | 0.50 | |
| Merocyanine of formula MC-11 | | | | 0.50 |
| Phenylbenzimidazole Sulfonic Acid | 1.00 | 1.00 | 1.00 | 1.00 |
| NaOH 45% | 0.30 | 0.30 | 0.30 | 0.30 |
| EDTA Solution | 1.00 | 1.00 | 1.00 | 1.00 |
| Preservatives, Parfum, Dyes | q.s. | q.s. | q.s. | q.s. |
| Water | ad 100 | ad 100 | ad 100 | ad 100 |

| Examples 19.1 | % b.w. | % b.w. | % b.w. | % b.w. |
|---|---|---|---|---|
| PEG-30 Dipolyhydroxystearate | 6.00 | 6.00 | 6.00 | 6.00 |
| Cetyl Dimethicone Copolyol | 6.00 | 6.00 | 6.00 | 6.00 |
| Mineral Oil | 4.00 | 4.00 | 4.00 | 4.00 |
| Caprylic Acid/Capric Acid Triglyceride | 6.00 | 6.00 | 6.00 | 6.00 |
| $C_{12-15}$ Alkylbenzoate | 5.00 | 5.00 | 5.00 | 5.00 |
| Butylene Glycol Dicaprylate/Dicaprate | 10.00 | 10.00 | 10.00 | 10.00 |
| Glycerin | 5.00 | 5.00 | 5.00 | 5.00 |
| $MgSO_4$ | 0.70 | 0.70 | 0.70 | 0.70 |
| Laurylethersulfate | 0.20 | 0.20 | 0.20 | 0.20 |
| Butyl Methoxydibenzoylmethane | 2.00 | 2.00 | 2.00 | 2.00 |
| Merocyanine of formula MC-08 | 8.00 | | | |
| Merocyanine of formula MC-09 | | 8.00 | | |
| Merocyanine of formula MC-10 | | | 8.00 | |
| Merocyanine of formula MC-11 | | | | 8.00 |
| 4-Methylbenzylidene Camphor | 4.00 | 4.00 | 4.00 | 4.00 |
| BEMBT | 2.00 | 2.00 | 2.00 | 2.00 |
| Phenylbenzimidazole Sulfonic Acid | 1.00 | 1.00 | 1.00 | 1.00 |
| NaOH 45% | 0.30 | 0.30 | 0.30 | 0.30 |
| EDTA Solution | 1.00 | 1.00 | 1.00 | 1.00 |
| Preservatives, Parfum, Dyes | q.s. | q.s. | q.s. | q.s. |
| Water | ad 100 | ad 100 | ad 100 | ad 100 |

| Examples 20.1 | % b.w. | % b.w. | % b.w. | % b.w. |
|---|---|---|---|---|
| PEG-30 Dipolyhydroxystearate | 6.00 | 6.00 | 6.00 | 6.00 |
| Cetyl Dimethicone Copolyol | 6.00 | 6.00 | 6.00 | 6.00 |
| Mineral Oil | 4.00 | 4.00 | 4.00 | 4.00 |
| Caprylic Acid/Capric Acid Triglyceride | 6.00 | 6.00 | 6.00 | 6.00 |
| $C_{12-15}$ Alkylbenzoate | 5.00 | 5.00 | 5.00 | 5.00 |
| Butylene Glycol Dicaprylate/Dicaprate | 10.00 | 10.00 | 10.00 | 10.00 |
| Glycerin | 5.00 | 5.00 | 5.00 | 5.00 |
| $MgSO_4$ | 0.70 | 0.70 | 0.70 | 0.70 |
| Sodiumisostearoyllactylate | 0.20 | 0.20 | 0.20 | 0.20 |
| Butyl Methoxydibenzoylmethane | 2.00 | 2.00 | 2.00 | 2.00 |
| Merocyanine of formula MC-08 | 4.00 | | | |
| Merocyanine of formula MC-09 | | 4.00 | | |
| Merocyanine of formula MC-10 | | | 4.00 | |
| Merocyanine of formula MC-11 | | | | 4.00 |
| 4-Methylbenzylidene Camphor | 4.00 | 4.00 | 4.00 | 4.00 |
| BEMBT | 2.00 | 2.00 | 2.00 | 2.00 |
| Phenylbenzimidazole Sulfonic Acid | 1.00 | 1.00 | 1.00 | 1.00 |
| NaOH 45% | 0.30 | 0.30 | 0.30 | 0.30 |
| EDTA Solution | 1.00 | 1.00 | 1.00 | 1.00 |
| Preservatives, Parfum, Dyes | q.s. | q.s. | q.s. | q.s. |
| Water | ad 100 | ad 100 | ad 100 | ad 100 |

| Example 21.1: Hydrodispersion Gel | % b.w. | % b.w. | % b.w. | % b.w. |
|---|---|---|---|---|
| Crosslinked Acrylic Acid/($C_{10-30}$) Alkyl Acrylate Copolymer | 0.50 | 0.50 | 0.50 | 0.50 |
| Ethanol | 3.50 | 3.50 | 3.50 | 3.50 |
| Glycerin | 3.00 | 3.00 | 3.00 | 3.00 |
| Dimethicone | 1.50 | 1.50 | 1.50 | 1.50 |
| Octyldodecanol | 0.50 | 0.50 | 0.50 | 0.50 |
| Caprylic Acid/Capric Acid Triglyceride | 5.00 | 5.00 | 5.00 | 5.00 |
| Bees wax | 2.00 | 2.00 | 2.00 | 2.00 |
| Butyl Methoxydibenzoylmethane (Parsol 1789) | 5.00 | 5.00 | 5.00 | 5.00 |
| Merocyanine of formula MC-08 | 1.50 | | | |
| Merocyanine of formula MC-09 | | 1.50 | | |
| Merocyanine of formula MC-10 | | | 1.50 | |
| Merocyanine of formula MC-11 | | | | 1.50 |
| Carbomer | 0.20 | 0.20 | 0.20 | 0.20 |
| NaOH 45% | 0.55 | 0.55 | 0.55 | 0.55 |
| Preservatives | q.s. | q.s. | q.s. | q.s. |
| Parfum | q.s. | q.s. | q.s. | q.s. |
| Water deion. | ad 100 | ad 100 | ad 100 | ad 100 |

| Example 22.1: W/O Lotion | % b.w. | % b.w. | % b.w. | % b.w. |
|---|---|---|---|---|
| Glycerylstearate SE | 3.50 | 3.50 | 3.50 | 3.50 |
| Stearic Acid | 1.80 | 1.80 | 1.80 | 1.80 |
| Glycerin | 3.00 | 3.00 | 3.00 | 3.00 |
| Cetearyl Alcohol | 0.50 | 0.50 | 0.50 | 0.50 |
| Octyldodecanol | 7.00 | 7.00 | 7.00 | 7.00 |
| Dicaprylyl Ether | 8.00 | 8.00 | 8.00 | 8.00 |
| Butyl Methoxydibenzoylmethane (Parsol 1789) | 3.00 | 3.00 | 3.00 | 3.00 |
| Synthetic Bees wax | 1.00 | 1.00 | 1.00 | 1.00 |
| Merocyanine of formula MC-08 | 2.50 | | | |
| Merocyanine of formula MC-09 | | 2.50 | | |
| Merocyanine of formula MC-10 | | | 2.50 | |
| Merocyanine of formula MC-11 | | | | 2.50 |
| Carbomer | 0.20 | 0.20 | 0.20 | 0.20 |
| NaOH 45% | 0.20 | 0.20 | 0.20 | 0.20 |
| Preservatives | q.s. | q.s. | q.s. | q.s. |
| Parfum | q.s. | q.s. | q.s. | q.s. |
| Water deion. | ad 100 | ad 100 | ad 100 | ad 100 |

| Example 23.1: O/W Lotion | % b.w. | % b.w. | % b.w. | % b.w. |
|---|---|---|---|---|
| Glycerylstearate SE | 3.50 | 3.50 | 3.50 | 3.50 |
| Stearic Acid | 1.80 | 1.80 | 1.80 | 1.80 |
| Glycerin | 3.00 | 3.00 | 3.00 | 3.00 |
| Cetearyl al | 0.50 | 0.50 | 0.50 | 0.50 |
| Octyldodecanol | 7.00 | 7.00 | 7.00 | 7.00 |
| Dicaprylyl Ether | 8.00 | 8.00 | 8.00 | 8.00 |
| Butyl Methoxydibenzoylmethane (Parsol 1789) | 3.00 | 3.00 | 3.00 | 3.00 |
| Synthetic Bees wax | 1.00 | 1.00 | 1.00 | 1.00 |
| Merocyanine of formula MC-08 | 2.00 | | | |
| Merocyanine of formula MC-09 | | 2.00 | | |
| Merocyanine of formula MC-10 | | | 2.00 | |
| Merocyanine of formula MC-11 | | | | 2.00 |
| Carbomer | 0.20 | 0.20 | 0.20 | 0.20 |
| NaOH 45% | 0.20 | 0.20 | 0.20 | 0.20 |
| Preservatives | q.s. | q.s. | q.s. | q.s. |
| Parfum | q.s. | q.s. | q.s. | q.s. |
| Water deion. | ad 100 | ad 100 | ad 100 | ad 100 |

| Example 24.1: Hydrodispersion Gel | % b.w. | % b.w. | % b.w. | % b.w. |
|---|---|---|---|---|
| Crosslinked Acrylic Acid/($C_{10-30}$) Alkyl Acrylate Copolymer | 0.50 | 0.50 | 0.50 | 0.50 |
| Ethanol | 3.50 | 3.50 | 3.50 | 3.50 |
| Glycerin | 3.00 | 3.00 | 3.00 | 3.00 |
| Dimethicone | 1.50 | 1.50 | 1.50 | 1.50 |
| Octyldodecanol | 0.50 | 0.50 | 0.50 | 0.50 |
| Caprylic Acid/Capric Acid Triglyceride | 5.00 | 5.00 | 5.00 | 5.00 |
| Synthetic Bees wax | 2.00 | 2.00 | 2.00 | 2.00 |
| Butyl Methoxydibenzoylmethane (Parsol 1789) | 5.00 | 5.00 | 5.00 | 5.00 |
| Merocyanine of formula MC-08 | 3.00 | | | |
| Merocyanine of formula MC-09 | | 3.00 | | |
| Merocyanine of formula MC-10 | | | 3.00 | |
| Merocyanine of formula MC-11 | | | | 3.00 |
| Carbomer | 0.20 | 0.20 | 0.20 | 0.20 |
| NaOH 45% | 0.55 | 0.55 | 0.55 | 0.55 |
| Preservatives | q.s. | q.s. | q.s. | q.s. |
| Parfum | q.s. | q.s. | q.s. | q.s. |
| Water deion. | ad 100 | ad 100 | ad 100 | ad 100 |

| Example 25.1 | [g] | [g] | [g] | [g] |
|---|---|---|---|---|
| Mixture of mono- and distearate of Glycerol/PEG 100 Stearate | 2.00 | 2.00 | 2.00 | 2.00 |
| Stearyl Alcohol | 1.00 | 1.00 | 1.00 | 1.00 |
| Stearic Acid of Palme Oil | 2.50 | 2.50 | 2.50 | 2.50 |
| Polydimethylsiloxane | 0.50 | 0.50 | 0.50 | 0.50 |
| $C_{12-15}$ Alkylbenzoate | 20.00 | 20.00 | 20.00 | 20.00 |
| Triethanolamine | 0.50 | 0.50 | 0.50 | 0.50 |
| Butyl Methoxydibenzoylmethane | 2.00 | 2.00 | 2.00 | 2.00 |
| Glycerin | 4.00 | 4.00 | 4.00 | 4.00 |
| Merocyanine of formula MC-08 | 0.40 | | | |
| Merocyanine of formula MC-09 | | 0.40 | | |
| Merocyanine of formula MC-10 | | | 0.40 | |
| Merocyanine of formula MC-11 | | | | 0.40 |
| Triethanolamine | 0.30 | 0.30 | 0.30 | 0.30 |
| Polyacrylic acid | 0.30 | 0.30 | 0.30 | 0.30 |
| Preservatives | q.s. | q.s. | q.s. | q.s. |
| Water demin. | ad 100 | ad 100 | ad 100 | ad 100 |

| Example 26.1 | | [g] | [g] | [g] | [g] |
|---|---|---|---|---|---|
| Phase A | Octocrylene | 9.00 | 9.00 | 9.00 | 9.00 |
| | Butyl Methoxydibenzoylmethane | 2.50 | 2.50 | 2.50 | 2.50 |
| | Dromtrizole Trisiloxane | 0.75 | 0.75 | 0.75 | 0.75 |
| | Decylcocoate | 9.00 | 9.00 | 9.00 | 9.00 |
| Phase B | Copolymer of acrylamide-2-methyl-2-propanesulfonic acid andn-dodecylamide 3.5%/99.5%) | 1.50 | 1.50 | 1.50 | 1.50 |
| Phase C | Glycerin | 4.00 | 4.00 | 4.00 | 4.00 |
| | Propylene glycol | | | | |
| | EDTA disodium salt | 0.10 | 0.10 | 0.10 | 0.10 |
| | Preservatives | q.s. | q.s. | q.s. | q.s. |
| | 4-Methylbenzylidene Camphor | 1.50 | 1.50 | 1.50 | 1.50 |
| | Triethanolamine | 0.26 | 0.26 | 0.26 | 0.26 |
| | Water | ad 100 | ad 100 | ad 100 | ad 100 |
| Phase D | Coated Titanium Dioxide | 16.7 | 16.7 | 16.7 | 16.7 |
| | Merocyanine of formula MC-08 | 2.00 | | | |
| | Merocyanine of formula MC-09 | | 2.00 | | |
| | Merocyanine of formula MC-10 | | | 2.00 | |
| | Merocyanine of formula MC-11 | | | | 2.00 |

| Example 27.1 | [g] | [g] | [g] | [g] |
|---|---|---|---|---|
| $C_{12-15}$ Alkylbenzoate | 10.00 | 10.00 | 10.00 | 10.00 |
| Methylene Bis-Benzotriazolyl Tetramethylbutyl-phenol in micronized form (Tinosorb M) | 2.50 | 2.50 | 2.50 | 2.50 |
| Octocrylene | 5.00 | 5.00 | 5.00 | 5.00 |
| Butyl Methoxydibenzoylmethane | 2.00 | 2.00 | 2.00 | 2.00 |
| Crosslinked Acrylic Acid/($C_{10-30}$) Alkyl Acrylate Copolymer | 0.75 | 0.75 | 0.75 | 0.75 |
| Titanium Dioxide | 3.00 | 3.00 | 3.00 | 3.00 |
| EDTA | 0.10 | 0.10 | 0.10 | 0.10 |
| 4-Methylbenzylidene Camphor | 0.50 | 0.50 | 0.50 | 0.50 |
| Glycerin | 5.00 | 5.00 | 5.00 | 5.00 |
| Merocyanine of formula MC-08 | 2.50 | | | |
| Merocyanine of formula MC-09 | | 2.50 | | |
| Merocyanine of formula MC-10 | | | 2.50 | |

| Example 27.1 | [g] | [g] | [g] | [g] |
|---|---|---|---|---|
| Merocyanine of formula MC-11 | | | | 2.50 |
| Triethanolamine | q.s. | q.s. | q.s. | q.s. |
| Water demin. | ad 100 | ad 100 | ad 100 | ad 100 |

Example 28.1-28.2

| | 28.1 | 28.2 | 28.1 | 28.2 | 28.1 | 28.2 | 28.1 | 28.2 |
|---|---|---|---|---|---|---|---|---|
| Emulsion Type | W/O | O/W | W/O | O/W | W/O | O/W | W/O | O/W |
| Titanium Dioxide | 2.00 | 2.00 | 2.00 | 2.00 | 2.00 | 2.00 | 2.00 | 2.00 |
| Stannous Oxide | | 4 | | 4 | | 4 | | 4 |
| Talcum | 2.00 | | 2.00 | | 2.00 | | 2.00 | |
| Boron Nitride | | 2.00 | | 2.00 | | 2.00 | | 2.00 |
| Dioctyl Succinate | | | | | | | | |
| Caprylic Acid/Capric Acid Triglyceride | 5.00 | 12.00 | 5.00 | 12.00 | 5.00 | 12.00 | 5.00 | 12.00 |
| Butylene Glycol Dicaprylate/ Dicaprate | 10.00 | 20.00 | 10.00 | 20.00 | 10.00 | 20.00 | 10.00 | 20.00 |
| $C_{12-15}$ Alkylbenzoate | 10.00 | 20.00 | 10.00 | 20.00 | 10.00 | 20.00 | 10.00 | 20.00 |
| Isohexadecane | 1.00 | | 1.00 | | 1.00 | | 1.00 | |
| Dicaprylyl Ether | 1.00 | | 1.00 | | 1.00 | | 1.00 | |
| Cyclomethicone | 1.00 | 2.00 | 1.00 | 2.00 | 1.00 | 2.00 | 1.00 | 2.00 |
| 4-Methylbenzylidene Camphor | 3.00 | 2.00 | 3.00 | 2.00 | 3.00 | 2.00 | 3.00 | 2.00 |
| Octyltriazone | 1.00 | 1.00 | 1.00 | 1.00 | 1.00 | 1.00 | 1.00 | 1.00 |
| Butyl Methoxydibenzoylmethane | 2 | 2 | 2 | 2 | 2 | 2 | 2 | 2 |
| Merocyanine of formula MC-08 | 3.00 | | | | | | | |
| Merocyanine of formula MC-08 | | 3.50 | | | | | | |
| Merocyanine of formula MC-09 | | | 3.00 | | | | | |
| Merocyanine of formula MC-09 | | | | 3.50 | | | | |
| Merocyanine of formula MC-10 | | | | | 3.00 | | | |
| Merocyanine of formula MC-10 | | | | | | 3.50 | | |
| Merocyanine of formula MC-11 | | | | | | | 3.00 | |
| Merocyanine of formula MC-11 | | | | | | | | 3.50 |
| Dioctylbutylalcohol | 2.00 | 8.00 | 2.00 | 8.00 | 2.00 | 8.00 | 2.00 | 8.00 |
| $C_{16-18}$ Alkylhydroxystearoylstearate | 1.00 | | 1.00 | | 1.00 | | 1.00 | |

Example 29.1-29.2

| | 29.1 | 29.2 | 29.1 | 29.2 | 29.1 | 29.2 | 29.1 | 29.2 |
|---|---|---|---|---|---|---|---|---|
| Emulsion Type | W/O | O/W | W/O | O/W | W/O | O/W | W/O | O/W |
| Titanium Dioxide | 2.00 | 2.00 | 2.00 | 2.00 | 2.00 | 2.00 | 2.00 | 2.00 |
| Stannous Oxide | | 4 | | 4 | | 4 | | 4 |
| Talcum | 2.00 | | 2.00 | | 2.00 | | 2.00 | |
| Boron Nitride | | 2.00 | | 2.00 | | 2.00 | | 2.00 |
| Caprylic Acid/Capric Acid Triglyceride | 5.00 | 12.00 | 5.00 | 12.00 | 5.00 | 12.00 | 5.00 | 12.00 |
| Butylene Glycol Dicaprylate/ Dicaprate | 10.00 | 20.00 | 10.00 | 20.00 | 10.00 | 20.00 | 10.00 | 20.00 |
| $C_{12-15}$ Alkylbenzoate | 10.00 | 20.00 | 10.00 | 20.00 | 10.00 | 20.00 | 10.00 | 20.00 |
| Isohexadecane | 1.00 | | 1.00 | | 1.00 | | 1.00 | |
| Dicaprylyl Ether | 1.00 | | 1.00 | | 1.00 | | 1.00 | |
| Cyclomethicone | 1.00 | 2.00 | 1.00 | 2.00 | 1.00 | 2.00 | 1.00 | 2.00 |
| 4-Methylbenzylidene Camphor | 3.00 | 2.00 | 3.00 | 2.00 | 3.00 | 2.00 | 3.00 | 2.00 |
| Octyltriazone | 1.00 | 1.00 | 1.00 | 1.00 | 1.00 | 1.00 | 1.00 | 1.00 |
| Butyl Methoxydibenzoylmethane | 2 | 2 | 2 | 2 | 2 | 2 | 2 | 2 |
| Merocyanine of formula MC-08 | 3.00 | | | | | | | |
| Merocyanine of formula MC-08 | | 3.50 | | | | | | |
| Merocyanine of formula MC-09 | | | 3.00 | | | | | |
| Merocyanine of formula MC-09 | | | | 3.50 | | | | |
| Merocyanine of formula MC-10 | | | | | 3.00 | | | |
| Merocyanine of formula MC-10 | | | | | | 3.50 | | |
| Merocyanine of formula MC-11 | | | | | | | 3.00 | |
| Merocyanine of formula MC-11 | | | | | | | | 3.50 |
| Dioctylbutylalcohol | 2.00 | 8.00 | 2.00 | 8.00 | 2.00 | 8.00 | 2.00 | 8.00 |
| $C_{16-18}$ Alkylhydroxystearoylstearate | 1.00 | | 1.00 | | 1.00 | | 1.00 | |

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_3$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctyl-stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially (aurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, ammonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene).

Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethyl-ammonium glycinates, cocoaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropyl-methylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 alkyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/ vinyl isodecanoate crosspolymer), Pemulen TR-1 (acrylates/ C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quarternised vinylpyrrolidone/ vinyl imidazole polymers, for example Luviquat® (BASF), condensation products of polyglycols and amines, quaternised collagen polypeptides, for example lauryldimonium hydroxypropyl hydrolyzed collagen (Lamequat° L/Grunau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/ Chemviron), polyaminopolyamides, as described, for example, in FR-A-2 252 840, and the cross-linked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/ methyl methacrylatetert-butylaminoethyl methacrylate/2-hydroxypropyl methacrylate copolymers, polyvinylpyrrolidone, vinylpyrrolidone/-vinyl acetate copolymers, vinyl pyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, anti-perspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such anti-oxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, heptathionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxy-phenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical olivoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylol-propane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-14), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Farbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased. (EP0893119). Some beads, as mentioned previously, provide a soft feel during spreading. Moreover, the optical activity of such beads, e.g. Micropearl M305, cans modulate skin shine by eliminating reflection phenomena and indirectly may scatter the UV light.

Other Adjuvants alpha glucosylrutin (CAS No. 130603-71-3), 2-butyloctyl o-hydroxybenzoate (CAS No. 190085-41-7), vitamin E (CAS No. 1406-18-4), vitamin E acetate (CAS No. 58-95-7), diethylhexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or iminodisuccinic acid and imiondisuccinic acid salts [CAS 7408-20-0] or latex particles, aloe vera, chamomile, ginko biloba, ginseng, coenzyme Q10, laminaria ochroleuca extract, magnolia oborata extract, melalenca alternifolia leaf oil, rubus idaeus seed oil, *vaccinium* macrocarpon seed oil, pumpkin seed extract, pumpkin seed oil, grape seed extract, carnosine, alpha-arbutin, madecassoside, termino-laside, tetrahydrocurcuminoids (THC), mycosporines, mycosporine like amino acids from the red alga *porphyra umbilicalis*, mycosporine-like amino acids (as described in WO2002039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO0341675 and linear poly-alpha-glucans as described in U.S. Pat. No. 6,616,935

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:
- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up, in the form of a stick,
- in the form of a spray (spray with propellent gas or pump-action spray) or an aerosol,
- in the form of a foam, or
- in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The following examples illustrate the invention.

APPLICATION EXAMPLES

Example 1

Sunscreen Formulations

Formulations are prepared according to the following table containing 2% of Butyl Methoxy Dibenzoyl Methane (BM-DBM) and 2% of one of the merocyanines MC08, MC09 or MC10. A fifth formulation served as the control containing only 2% BMDBM without a merocyanine.

|        | INCI name                                                                              | % b.w.   |
|--------|----------------------------------------------------------------------------------------|----------|
| Part A | Potassium Cetyl Phosphate                                                              | 1.80     |
|        | Glyceryl Stearate                                                                      | 2.50     |
|        | Stearyl Alcohol                                                                        | 2.50     |
|        | Mineral Oil                                                                            | 5.00     |
|        | Merocyanine UV absorbere MC08, MC09 or MC10 *)                                         | 2.00     |
|        | Butyl Methoxy Dibenzolymethane                                                         | 2.00     |
|        | $C_{12}$-$C_{15}$ Alkyl Benzoate                                                        | 8.00     |
| Part B | Aqua                                                                                   | ad 100   |
|        | Xanthan Gum                                                                            | 0.30     |
|        | Glycerin                                                                               | 10.00    |
| Part C | Phenoxyethanol (and) Methylparaben (and) Ethylparaben (and) Butylparaben (and) Propylparaben (and) Isobutylparaben | 0.80     |

Part A and part B are prepared separately and heated up to 75° C.
Under increasing stirring part B is incorporated into part A with Ultra Turrax for 10 sec. at 10 000 rpm.
The pH is adjusted at room temperature after cooling down under stirring.
*) If no merocyanine is used, the concentration of C12-15 Alkyl Benzoate is set to 10% (instead of 8% in the presence of 2% of a merocyanine).

Example 2

Photostability Experiments

For photostability assessment 2 mg/cm$^2$ of the respective formulation described in Example 1 are spread on roughened quartz plates. The samples are irradiated using an Atlas CPS+ solar simulator. The temperature of the samples is kept between 35 and 40° C. by cooling of the sample support. The CPS+device is operated with 760 W/m$^2$ total intensity corresponding to 5 MED (MED=minimal erythema) dose) per hour. After irradiation, the samples are analyzed quantitatively with respect to the parent substance by HPLC methods. For each formulation at each UV-dose seven plates are taken and the results of those seven plates are averaged.

The recovery of BMDBM at 20 MED is shown together with the standard deviation (n=7) in the following Table:

| UV-absorbers in formulation | Recovery of BMDBM after 20 MED ± standard deviation (n = 7) |
|---|---|
| 2% Butyl Methoxydibenzoylmethane + 2% of the compound of formula (MC 08) | (67 ± 3) % |
| 2% Butyl Methoxydibenzoylmethane + 2% of the compound of formula (MC 10) | (46 ± 8) % |
| 2% Butyl Methoxydibenzoylmethane + 2% of the compound of formula (MC 09) | (33 ± 4) % |
| 2% Butyl Methoxydibenzoylmethane | (1 ± 1) % |

In FIG. 1 the results are shown in terms of recovery of Butyl Methoxydibenzoylmethane without any further UV-absorber present and in the presence of the compound of formulae (MC 08), (MC 09) and (MC 10).

There is a significant stabilization of Butyl Methoxydibenzoylmethane in the presence of the merocyanine compound.

The invention claimed is:

1. A method of stabilizing organic UV-sensitive active ingredients selected from a dibenzoylmethane derivative by adding a merocyanine derivative of formula

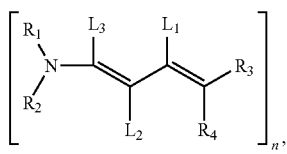

wherein $L_1$, $L_2$ or $L_3$ independently of each other hydrogen; hydroxy; $C_1$-$C_{22}$alkyl; $C_1$-$C_{22}$alkoxy; $C_2$-$C_{22}$alkenyl; $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl, $C_4$-$C_{20}$heteroaralkyl; $C_6$-$C_{18}$aryl;

$R_4$ is CN; —$COR_5$; —$COOR_5$; —$CONR_5R_6$; $C_2$-$C_{22}$alkenyl; $C_2$-$C_{22}$alkinyl; $C_3$-$C_{12}$cycloalkyl; $C_6$-$C_{18}$aryl; $C_3$-$C_{12}$heteroaryl; $C_2$-$C_{12}$heteroalkyl; or $C_3$-$C_5$heterocycloalkyl;

$R_5$, $R_6$, $R_7$ and $R_8$ are independently of each other hydrogen; $C_1$-$C_{22}$alkyl, $C_2$-$C_{22}$alkenyl, $C_2$-$C_{22}$alkinyl; $C_3$-$C_{12}$cycloalkyl; $C_3$-$C_{12}$cycloalkenyl; $C_7$-$C_{20}$ aralkyl; $C_1$-$C_{20}$heteroalkyl; $C_3$-$C_{12}$cycloheteroalkyl; $C_5$-$C_{20}$heteroaralkyl; $C_6$-$C_{18}$aryl; $C_3$-$C_{12}$heteroaryl; —$(CH_2)_u$—$SiR_{16}R_{17}R_{18}$; or a radical —X-Sil; or $L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $R_3$ and $R_4$, $R_1$ and $R_2$, $R_5$ and $R_6$, and $R_7$ and $R_8$ may be linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups;

and each alkyl, alkenyl, alkinyl, cycloalkyl or cycloalkylene group may be unsubstituted or substituted by one or more $R_{10}$;

and each aryl, heteroaryl, aralkyl, arylene, heteroarylene or aralkylene may be unsubstituted or substituted by one or more $R_{11}$;

$R_9$ is $R_{12}$; $COR_{12}$, $COOR_{12}$; or $CONR_{12}R_{13}$;

$R_{10}$ is halogen, OH; $NR_{14}R_{15}$; O—$R_{14}$; S—$R_{14}$; CO—$R_{14}$; O—CO—$R_{14}$; oxo; thiono; ($C_1$-$C_6$)alkylidene; CN; $COOR_{14}$; $CONR_{14}R_{15}$; $SO_2NR_{14}R_{15}$; $SO_2R_{14}$; $SO_3R_{14}$; $SiR_{16}R_{17}R_{18}$; $OSiR_{16}R_{17}R_{18}$; $POR_{16}R_{17}$; or a radical —X-Sil;

$R_{11}$ is $C_1$-$C_{12}$alkylthio; $C_3$-$C_{12}$cycloalkylthio; $C_1$-$C_{12}$alkenylthio; $C_3$-$C_{12}$cycloalkenylthio; $C_1$-$C_{22}$alkoxy; $C_3$-$C_{12}$cycloalkoxy; $C_1$-$C_{12}$alkenyloxy; or $C_3$-$C_{12}$cycloalkenyloxy which may be unsubstituted or substituted by one or more $R_9$; halogen; CN; SH; OH; CHO; $R_{19}$; $OR_{19}$; $SR_{19}$; $C(R_{19})$=$CR_{19}R_{20}$; O—CO—$R_{19}$; $NR_{19}R_{20}$; $CONR_{19}R_{20}$; $SO_2NR_{19}R_{20}$; $SO_2R_{19}$; $COOR_{19}$, $OCOOR_{19}$; $NR_{19}COR_{20}$; $NR_{19}COOR_{20}$; $SiR_{16}R_{17}R_{18}$; $OSiR_{16}R_{17}R_{18}$; P(=O)$R_{16}R_{17}$; or a radical —X-Sil;

$R_{16}$, $R_{17}$ and $R_{18}$ independently form each other are $C_1$-$C_{22}$alkyl; $C_5$-$C_{18}$aryl; or $C_1$-$C_{22}$alkoxy;

$R_{12}$, $R_{13}$, $R_{14}$, $R_{15}$, $R_{19}$ and $R_{20}$ independently of each other are hydrogen; $C_1$-$C_{22}$alkyl; $C_3$-$C_{12}$cycloalkyl; $C_2$-$C_{12}$alkenyl; $C_3$-$C_{12}$cycloalkenyl; $C_6$-$C_{18}$aryl; $C_3$-$C_{12}$heteroaryl; $C_7$-$C_{20}$aralkyl; or $C_4$-$C_{20}$heteroaralkyl; or $R_{12}$ and $R_{13}$, $R_{14}$ and $R_{15}$, and/or $R_{19}$ and $R_{20}$ may be linked together to form unsubstituted or $C_1$-$C_4$alkyl-substituted pyrrolidine, piperidine, piperazine or morpholine;

X is a linker; and

Sil is a silane-, oligosiloxane or polysiloxane moiety;

if n=1

$R_1$ and $R_2$ independently of each other hydrogen; $C_1$-$C_{22}$ alkyl; $C_2$-$C_{22}$alkenyl; $C_2$-$C_{22}$ alkinyl; $C_3$-$C_{12}$cycloalkyl; $C_3$-$C_{12}$cycloalkenyl; $C_7$-$C_{20}$aralkyl; $C_2$-$C_{20}$heteroalkyl; $C_3$-$C_{12}$cycloheteroalkyl; $C_6$-$C_{18}$aryl; $C_4$-$C_{20}$heteroaralkyl; $C_3$-$C_{12}$heteroaryl; —$(CH_2)_u$—$SiR_{16}R_{17}R_{18}$; or —X-Sil;

u is a number from 1 to 12;

$R_3$ is CN; —$COR_7$; —$COOR_7$; or —$CONR_7R_8$;

if n=2 one of $R_1$, $R_2$ and $R_3$ is a-bivalent radical; and two of $R_1$, $R_2$ and $R_3$ are defined as for n=1; or $R_1$ and $R_2$ together with the nitrogen atoms form a six-membered heterocyclic ring and simultaneously $R_3$ is defined as for n=1;

if n=3 one of $R_1$, $R_2$ and $R_3$ is a trivalent radical; and two of $R_1$, $R_2$ and $R_3$ are defined as for n=1;

if n=4 one of $R_1$, $R_2$ and $R_3$ is a tetravalent radical; and two of $R_1$, $R_2$ and $R_3$ are defined as for n=1;

to said active ingredients.

2. The method according to claim 1 wherein the compounds of formula (1) are in their E,E-, E,Z- or Z,Z-isomeric forms.

3. The method according to claim 1, wherein in formula (I) $L_1$ is hydrogen; or OH;

$R_3$ is —$COOR_7$; —$COR_7$; —$CONR_7R_8$; or —CN;

$L_2$ and $L_3$ independently from each other are hydrogen or $C_1$-$C_{22}$alkyl;

$R_4$ is cyano; $COR_5$, $COOR_5$; $CONR_5R_6$; $C_2$-$C_{12}$heteroalkyl; $C_3$-$C_5$heterocycloalkyl; $C_6$-$C_{18}$aryl; or $C_3$-$C_{12}$heteroaryl;

$R_1$ and $R_2$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_4$-$C_{20}$heteroaralkyl; $C_6$-$C_{18}$aryl; or $C_3$-$C_{12}$heteroaryl; or —X-Sil; or $L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $R_3$ and $R_4$, $R_1$ and $R_2$, $R_5$ and $R_6$, and $R_7$ and $R_8$ may be linked together to form 1, 2, 3 or 4 carbocyclic or heterocyclic rings, which may be uninterrupted or interrupted by one or more —O—, —S— or —$NR_9$— and/or which may be further fused with other aromatic rings and/or which may be substituted with one or more $C_1$-$C_6$alkyl groups;

n is 1; and $R_5$, $R_6$, $R_7$ and $R_8$ are defined as in claim 1.

4. The method according to claim 1, wherein $L_1$ is hydrogen; or OH;

$R_3$ is —$COOR_7$; —$COR_7$; —$CONR_7R_8$; or —CN;

$L_2$ and $L_3$ independently from each other are hydrogen;

$R_4$ is cyano; $COR_5$, $COOR_5$; $CONR_5R_6$;

$R_5$, $R_6$, $R_7$ and $R_8$ are independently of each other hydrogen; $C_1$-$C_{22}$alkyl, $C_2$-$C_{22}$alkenyl, $C_3$-$C_{12}$cycloalkyl; $C_1$-$C_{20}$heteroalkyl; $C_6$-$C_{18}$aryl; —$(CH_2)_u$—$SiR_{16}R_{17}R_{18}$; or a radical —X-Sil; and $R_1$ and $R_2$ independently from each other are hydrogen; $C_1$-$C_{22}$alkyl; or —X-Sil; or $L_1$ and $L_3$, $L_1$ and $R_4$, $L_3$ and $R_1$, $R_3$ and $R_4$, and $R_1$ and $R_2$, may be linked together to form 1, 2, 3 or 4 carbocyclic or heterocyclic rings, which may be uninterrupted or interrupted by one or more —O—, —S— or —NR$_9$— and/or which may be further fused with other aromatic rings and/or which may be substituted with one or more $C_1$-$C_6$alkyl groups;

n is 1; and $R_{16}$, $R_{17}$, $R_{18}$, X, Sil and u are defined as in claim 1.

5. The method according to claim 1, wherein $L_1$, $L_2$ and $L_3$ are hydrogen; or $L_1$ and $L_3$ are linked together to form a cyclohexene ring, which may be substituted with one or two methyl groups.

6. The method according to claim 1, wherein $R_1$ and $R_2$ together form a piperazine ring;

n is 2; and $L_1$, $L_2$, $L_3$, $R_3$ and $R_4$ are defined as in claim 1.

7. The method according to claim 1, wherein the merocyanine derivatives are selected from the compounds of formulae

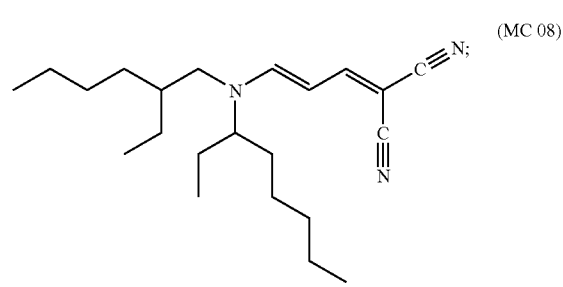
(MC 08)

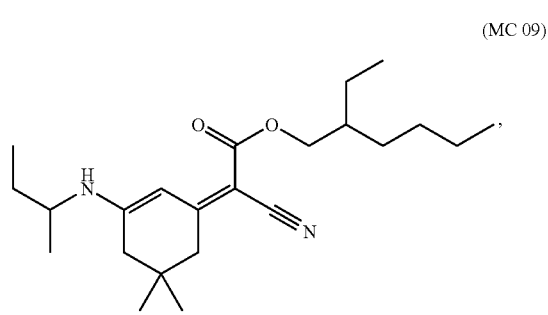
(MC 09)

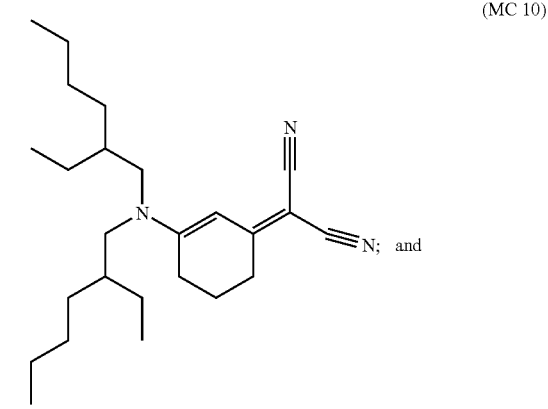
(MC 10)

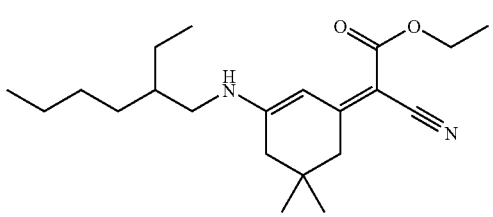
(MC 11)

8. The method according to claim 1 wherein the dibenzoylmethane derivative is 4-(tert-butyl)-4'-methoxydibenzoylmethane.

9. The method according to claim 1, wherein the compound of formula (1) is formula (MC 11)

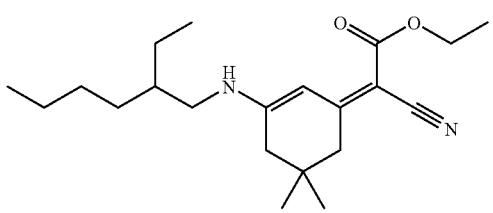 [SMILES: CCCCC(CC)CNC1=C/C(=C(/C#N)C(=O)OCC)CC(C)(C)C1]

and the dibenzoylmethane derivative is 4 (tert-butyl)-4'-methoxydibenzoylmethane.

10. A composition comprising at least one screening system in a physiologically acceptable support, characterized in that the screening system comprises:

(a) at least one UV sensitive ingredient selected from the group consisting of dibenzoylmethane derivative(s); and (b) at least one merocyanine derivative as defined according to claim 1.

11. The composition according to claim 10, in which the dibenzoylmethane derivative(s) is (are) present in amounts of 0.01% to 20% by weight with respect to the total composition weight.

12. The composition according to claim 10, in which the merocyanine derivative(s) is (are) present in amounts of 0.01% to 20% by weight with respect to the total composition weight.

13. The composition according to claim 10, characterized in that it constitutes a skin care product, a makeup product for the skin, a sun protection product or a skin cleansing product.

14. The composition according to claim 13, characterized in that it constitutes a sun protection product.

15. The composition according to claim 10, wherein the dibenzoylmethane derivative is 4-(tert-butyl)-4'-methoxydibenzoylmethane.

16. The composition according to claim 10, wherein the dibenzoylmethane derivative is 4-(tert-butyl)-4'-methoxydibenzoylmethane and the merocyanine derivatives are selected from the compounds of formulae

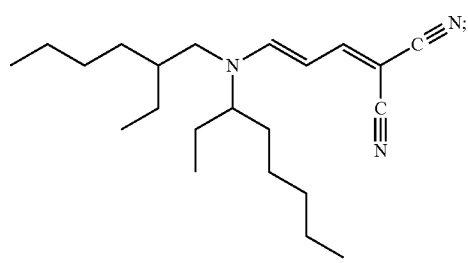
(MC 09)
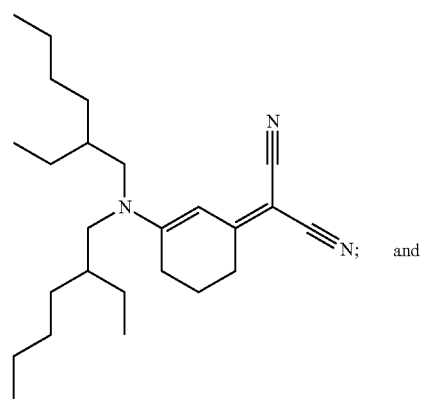
(MC 10)
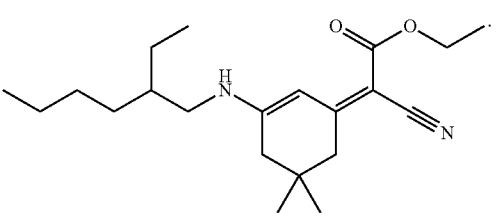
(MC 11)
* * * * *